US011118189B2

(12) United States Patent
Pennell et al.

(10) Patent No.: US 11,118,189 B2
(45) Date of Patent: Sep. 14, 2021

(54) METHODS FOR GENETIC MODIFICATION OF PLANTS

(71) Applicant: Ceres, Inc., Thousand Oaks, CA (US)

(72) Inventors: Roger I. Pennell, Thousand Oaks, CA (US); Richard Hamilton, Thousand Oaks, CA (US); Delin Liang, Thousand Oaks, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 15/781,044

(22) PCT Filed: Dec. 2, 2016

(86) PCT No.: PCT/US2016/064733
§ 371 (c)(1),
(2) Date: Jun. 1, 2018

(87) PCT Pub. No.: WO2017/096237
PCT Pub. Date: Jun. 8, 2017

(65) Prior Publication Data
US 2020/0299717 A1 Sep. 24, 2020

Related U.S. Application Data

(60) Provisional application No. 62/261,944, filed on Dec. 2, 2015.

(51) Int. Cl.
*C12N 15/82* (2006.01)
*A01H 1/04* (2006.01)
*A01H 1/02* (2006.01)
*C12N 9/22* (2006.01)
*C12N 15/11* (2006.01)

(52) U.S. Cl.
CPC .......... *C12N 15/8274* (2013.01); *A01H 1/02* (2013.01); *A01H 1/04* (2013.01); *C12N 9/22* (2013.01); *C12N 15/111* (2013.01); *C12N 15/8213* (2013.01); *C12N 15/8286* (2013.01); *C12N 2310/20* (2017.05); *C12Y 204/01012* (2013.01)

(58) Field of Classification Search
None
See application file for complete search history.

(56) References Cited

U.S. PATENT DOCUMENTS

2003/0208790 A1* 11/2003 Jansens ............... C12N 15/8286
800/279
2004/0060080 A1 3/2004 Tanaka et al.
2012/0096592 A1 4/2012 Hatzfeld
2015/0082478 A1* 3/2015 Cigan ................. C12N 15/8216
800/270

FOREIGN PATENT DOCUMENTS

WO 2006/124502 11/2006
WO WO-2014186686 A2 * 11/2014 ......... C12N 15/8216
WO 2015/131101 3/2015

OTHER PUBLICATIONS

Weeks et al 2008 (Transgenic Research 17: p. 587-597) (Year: 2008).*
Mao et al., "Development of germ-line specific CRISPR-Cas9 systems to improve the production of heritable gene modifications in *Arabidopsis*," Plant Biotechnology Journal 14(2):519-532, 2015.
Gao et al., "Auxin binding protein 1 (ABP1) is not required for either auxin signaling or *Arabidopsis* development," Proceedings of the National Academy of Sciences of the United States of America 112(7):2275-2280, 2015.
Kumar et al., "The CRISPR-Cas system for plant genome editing: advances and opportunities," Journal of Experimental Botany 66(1):47-57, 2015.
Extended European Search Report regarding Europe Patent Application No. 16871621.5 dated Apr. 5, 2019.
Danilevskaya, et al., "Involvement of the MADS-Box Gene ZMM4 in Floral Induction and Inflorescence Development in Maize," Plant Physiology, vol. 147, pp. 2054-2069 (2008).
Hemerly, et al., "Cell Division Events Are Essential for Embryo Patterning and Morphogenesis: Studies on Dominant-negative cdc2aAt Mutants of *Arabidopsis*," Plant Journal, vol. 23, pp. 123-130 (2000).
International Search Report and Written Opinion Regarding International Application No. PCT/US2016/064733 dated Jun. 5, 2018.
Kalluri, et al., "Systems and Synthetic Biology Approaches to Alter Plant Cell Walls and Reduce Biomass Recalcitrance," Plant Biotechnology Journal, vol. 12, pp. 1207-1216 (2014).
Mali, et al., "RNA-guided Human Genome Engineering via Cas9," Science 339(6121):823-826 (2013).
Zhang, "Transgenic Cotton Breeding," in Cotton, 2nd ed., Agron. Monogr. 57, pp. 229-254 (2015), ASA, CSSA, and SSSA, Madison, WI.
GenBank Accession No. AC211016, dated Sep. 13, 2014.
GenBank Accession No. CW083154, dated Feb. 5, 2014.

* cited by examiner

*Primary Examiner* — Matthew R Keogh
(74) *Attorney, Agent, or Firm* — Dentons US LLP

(57) ABSTRACT

Described are methods and materials for the genetic modification of plants by specific gene targeting and precise editing of nucleic acid sequences in a plant. The methods and materials provided herein enable one to edit the plant genome by design to control the expression of endogenous genes and/or control the transmission and expression of transgenic traits. Provided are also methods of producing plants having a desirable agronomic trait by crossing a transgenic plant expressing a gRNA with a plant expressing a Cas enzyme, and selecting a progeny plant having the desirable agronomic trait or a seed thereof.

20 Claims, 1 Drawing Sheet
Specification includes a Sequence Listing.

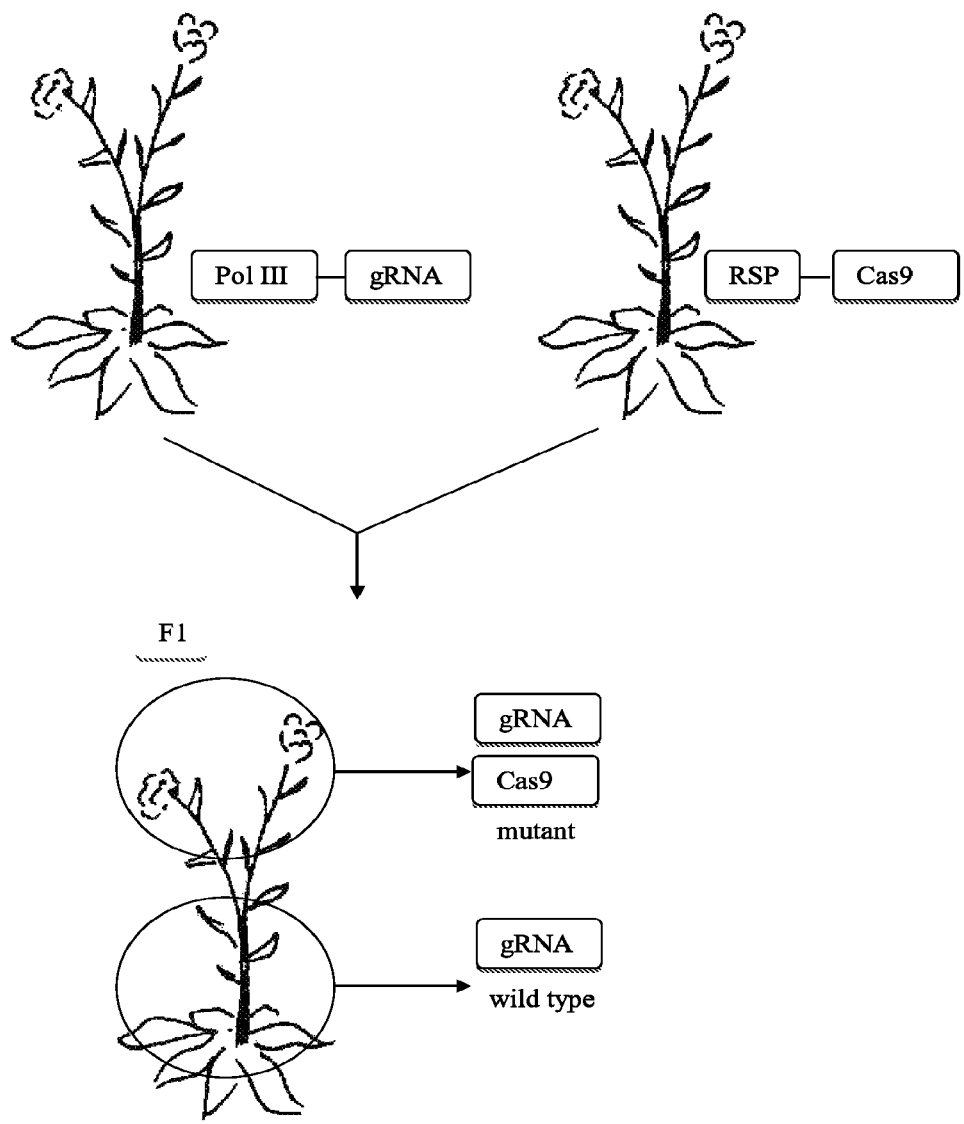

SEQUENCE LISTING

<160> NUMBER OF SEQ ID NOS: 16

<210> SEQ ID NO 1
<211> LENGTH: 4395
<212> TYPE: DNA
<213> ORGANISM: Streptococcus pyogenes

<400> SEQUENCE: 1

```
atgggcggta ggcgtgtacg gtgggaggtc tatataagca gagctcgttt agtgaaccgt     60
cagaattttg taatacgact cactataggg cggccgggaa ttcgtcgact ggaaccggta    120
ccgaggagat ctgccgccgc gatcgccatg gataagaaat actcaatagg actggatatt    180
ggcacaaata gcgtcggatg ggctgtgatc actgatgaat ataaggttcc ttctaaaaag    240
ttcaaggttc tgggaaatac agaccgccac agtatcaaaa aaaatcttat aggggctctt    300
ctgtttgaca gtggagagac agccgaagct actagactca aacggacagc taggagaagg    360
tatacaagac ggaagaatag gatttgttat ctccaggaga tttttttcaaa tgagatggcc    420 aaagtggatg atagtttctt tcatagactt gaagagtctt ttttggtgga agaagacaag    480
aagcatgaaa gacatcctat ttttggaaat atagtggatg aagttgctta tcacgagaaa    540
tatccaacta tctatcatct gagaaaaaaa ttggtggatt ctactgataa agccgatttg    600
```

```
cgcctgatct atttggccct ggcccacatg attaagttta gaggtcattt tttgattgag    660
ggcgatctga atcctgataa tagtgatgtg acaaactgt  ttatccagtt ggtgcaaacc    720
tacaatcaac tgtttgaaga aaaccctatt aacgcaagtg gagtggatgc taaagccatt    780
ctttctgcaa gattgagtaa atcaagaaga ctggaaaatc tcattgctca gctccccggt    840
gagaagaaaa atggcctgtt tgggaatctc attgctttgt cattgggttt gaccctaat     900 tttaaatcaa attttgattt ggcagaagat gctaaactcc agctttcaaa agatacttac    960
gatgatgatc tggataatct gttggctcaa attggggatc aatatgctga tttgtttttg   1020
gcagctaaga atctgtcaga tgctattctg ctttcagaca tcctgagagt gaatactgaa   1080
ataactaagg ctccctgtc  agcttcaatg attaaacgct acgatgaaca tcatcaagac   1140
ttgactcttc tgaaagccct ggttagacaa caacttccag aaaagtataa agaaatcttt   1200
tttgatcaat caaaaaacgg atatgcaggt tatattgatg gcggcgcaag ccaagaagaa   1260
ttttataaat ttatcaaacc aattctggaa aaaatggatg gtactgagga actgttggtg   1320
aaactgaata gagaagattt gctgcgcaag caacggacct tgacaacgg  ctctattccc   1380 catcaaattc acttgggtga gctgcatgct attttgagaa acaagaaga  cttttatcca   1440 tttctgaaag acaatagaga gaagattgaa aaaatcttga cttttaggat tccttattat   1500
gttggtccat tggccagagg caatagtagg tttgcatgga tgactcggaa gtctgaagaa   1560
acaattaccc catggaattt tgaagaagtt gtcgataaag gtgcttcagc tcaatcattt   1620
attgaacgca tgacaaactt tgataaaaat cttccaaatg aaaaagtgct gccaaaacat   1680
agtttgcttt atgagtattt taccgtttat aacgaattga caaaggtcaa atatgttact   1740
gaaggaatga aaaaccagc  atttctttca ggtgaacaga gaaagccat  tgttgatctg   1800 ctcttcaaaa caaataggaa agtgaccgtt aagcaactga agaagatta  tttcaaaaaa   1860 atagaatgtt ttgatagtgt tgaaatttca ggagttgaag atagatttaa tgcttcactg   1920
ggtacatacc atgatttgct gaaaattatt aaagataaag attttttgga taatgaagaa   1980
aatgaagaca tcctggagga tattgttctg acattgaccc tgtttgaaga tagggagatg   2040
attgaggaaa gacttaaaac atacgctcac ctctttgatg ataaggtgat gaaacagctt   2100
aaaagacgca gatatactgg ttggggaagg ttgtccagaa aattgattaa tggtattagg   2160
gataagcaat ctggcaaaac aatactggat ttttgaaat  cagatggttt tgccaatcgc   2220
aattttatgc agctcatcca tgatgatagt ttgacattta agaagacat  ccaaaaagca   2280 caagtgtctg acaaggcga  tagtctgcat gaacatattg caaatctggc tggtagccct   2340
gctattaaaa aaggtattct ccagactgtg aaagttgttg atgaattggt caaagtgatg   2400
gggcggcata agccagaaaa tatcgttatt gaaatggcaa gagaaaatca gacaactcaa   2460
aagggccaga aaattccag  agagaggatg aaagaatcg  agaaggtat  caagaactg    2520 ggaagtcaga ttcttaaaga gcatcctgtt gaaaatactc aattgcaaaa tgaaaagctc   2580
tatctctatt atctccaaaa tggaagagat atgtatgtgg accaagaact ggatattaac   2640
aggctgagtg attatgatgt cgatcacatt gttccacaaa gtttccttaa agacgattca   2700
atagacaata aggtcctgac caggtctgat aaaaatagag gtaaatccga taacgttcca   2760
agtgaagaag tggtcaaaaa gatgaaaaac tattggagac aacttctgaa cgccaagctg   2820
atcactcaaa ggaagtttga taatctgacc aaagctgaaa gaggaggttt gagtgaactt   2880
gataaagctg gttttatcaa acgccaattg gttgaaactc gccaaatcac taagcatgtg   2940
```

```
gcacaaattt tggatagtcg catgaatact aaatacgatg aaaatgataa acttattaga    3000
gaggttaaag tgattaccct gaaatctaaa ctggtttctg acttcagaaa agatttccaa    3060
ttctataaag tgagagagat taacaattac catcatgccc atgatgccta tctgaatgcc    3120
gtcgttggaa ctgctttgat taagaaatat ccaaaacttg aaagcgagtt tgtctatggt    3180
gattataaag tttatgatgt taggaaaatg attgctaagt ctgagcaaga aataggcaaa    3240
gcaaccgcaa agtatttctt ttactctaat atcatgaact tcttcaaaac agaaattaca    3300
cttgcaaatg gagagattcg caaacgccct ctgatcgaaa ctaatgggga aactggagaa    3360
attgtctggg ataaagggag agattttgcc acagtgcgca aagtgttgtc catgccccaa    3420
gtcaatatcg tcaagaaaac agaagtgcag acaggcggat tctctaagga gtcaattctg    3480
ccaaaaagaa attccgacaa gctgattgct aggaaaaaag actgggaccc aaaaaaatat    3540
ggtggttttg atagtccaac cgtggcttat tcagtcctgg tggttgctaa ggtggaaaaa    3600
gggaaatcca agaagctgaa atccgttaaa gagctgctgg ggatcacaat tatgaaaga     3660 agttcctttg aaaaaaatcc cattgacttt ctggaagcta aaggatataa ggaagttaaa    3720
aaagacctga tcattaaact gcctaaatat agtcttttg agctggaaaa cggtaggaaa     3780
cggatgctgg ctagtgccgg agaactgcaa aaggaaatg agctggctct gccaagcaaa     3840
tatgtgaatt ttctgtatct ggctagtcat tatgaaagt tgaagggtag tccagaagat      3900
aacgaacaaa acaattgtt tgtggagcag cataagcatt atctggatga gattattgag      3960
caaatcagtg aatttttctaa gagagttatt ctggcagatg ccaatctgga taaagttctt    4020
agtgcatata caaacatag agacaaacca ataagagaac aagcagaaaa tatcattcat      4080
ctgtttacct tgaccaatct tggagcaccc gctgcttta aatactttga taacaatt       4140 gataggaaaa gatataccta tacaaaagaa gttctggatg ccactcttat ccatcaatcc    4200
atcactggtc tttatgaaac acgcattgat ttgagtcagc tgggaggtga ccccaagaaa    4260
aaacgcaagg tggaagatcc taagaaaaag cggaaagtgg acacgcgtac gcggccgctc    4320
gagcagaaac tcatctcaga agaggatctg gcagcaaatg atatcctgga ttacaaggat    4380
gacgacgata aggtt                                                      4395
```

<210> SEQ ID NO 2
<211> LENGTH: 1465
<212> TYPE: PRT
<213> ORGANISM: Streptococcus pyogenes

<400> SEQUENCE: 2

```
Met Gly Gly Arg Arg Val Arg Trp Glu Val Tyr Ile Ser Arg Ala Arg
1               5                   10                  15

Leu Val Asn Arg Gln Asn Phe Val Ile Arg Leu Thr Ile Gly Arg Pro
            20                  25                  30

Gly Ile Arg Arg Leu Glu Pro Val Pro Arg Arg Ser Ala Ala Ala Ile
        35                  40                  45

Ala Met Asp Lys Lys Tyr Ser Ile Gly Leu Asp Ile Gly Thr Asn Ser
    50                  55                  60

Val Gly Trp Ala Val Ile Thr Asp Glu Tyr Lys Val Pro Ser Lys Lys
65                  70                  75                  80

Phe Lys Val Leu Gly Asn Thr Asp Arg His Ser Ile Lys Lys Asn Leu
                85                  90                  95

Ile Gly Ala Leu Leu Phe Asp Ser Gly Glu Thr Ala Glu Ala Thr Arg
            100                 105                 110
```

-continued

```
Leu Lys Arg Thr Ala Arg Arg Tyr Thr Arg Arg Lys Asn Arg Ile
        115                 120                 125
Cys Tyr Leu Gln Glu Ile Phe Ser Asn Glu Met Ala Lys Val Asp Asp
130                 135                 140
Ser Phe Phe His Arg Leu Glu Glu Ser Phe Leu Val Glu Glu Asp Lys
145                 150                 155                 160
Lys His Glu Arg His Pro Ile Phe Gly Asn Ile Val Asp Glu Val Ala
                165                 170                 175
Tyr His Glu Lys Tyr Pro Thr Ile Tyr His Leu Arg Lys Lys Leu Val
            180                 185                 190
Asp Ser Thr Asp Lys Ala Asp Leu Arg Leu Ile Tyr Leu Ala Leu Ala
        195                 200                 205
His Met Ile Lys Phe Arg Gly His Phe Leu Ile Glu Gly Asp Leu Asn
    210                 215                 220
Pro Asp Asn Ser Asp Val Asp Lys Leu Phe Ile Gln Leu Val Gln Thr
225                 230                 235                 240
Tyr Asn Gln Leu Phe Glu Glu Asn Pro Ile Asn Ala Ser Gly Val Asp
                245                 250                 255
Ala Lys Ala Ile Leu Ser Ala Arg Leu Ser Lys Ser Arg Arg Leu Glu
            260                 265                 270
Asn Leu Ile Ala Gln Leu Pro Gly Glu Lys Lys Asn Gly Leu Phe Gly
        275                 280                 285
Asn Leu Ile Ala Leu Ser Leu Gly Leu Thr Pro Asn Phe Lys Ser Asn
    290                 295                 300
Phe Asp Leu Ala Glu Asp Ala Lys Leu Gln Leu Ser Lys Asp Thr Tyr
305                 310                 315                 320
Asp Asp Asp Leu Asp Asn Leu Leu Ala Gln Ile Gly Asp Gln Tyr Ala
                325                 330                 335
Asp Leu Phe Leu Ala Ala Lys Asn Leu Ser Asp Ala Ile Leu Leu Ser
            340                 345                 350
Asp Ile Leu Arg Val Asn Thr Glu Ile Thr Lys Ala Pro Leu Ser Ala
        355                 360                 365
Ser Met Ile Lys Arg Tyr Asp Glu His His Gln Asp Leu Thr Leu Leu
    370                 375                 380
Lys Ala Leu Val Arg Gln Gln Leu Pro Glu Lys Tyr Lys Glu Ile Phe
385                 390                 395                 400
Phe Asp Gln Ser Lys Asn Gly Tyr Ala Gly Tyr Ile Asp Gly Gly Ala
                405                 410                 415
Ser Gln Glu Glu Phe Tyr Lys Phe Ile Lys Pro Ile Leu Glu Lys Met
            420                 425                 430
Asp Gly Thr Glu Glu Leu Leu Val Lys Leu Asn Arg Glu Asp Leu Leu
        435                 440                 445
Arg Lys Gln Arg Thr Phe Asp Asn Gly Ser Ile Pro His Gln Ile His
    450                 455                 460
Leu Gly Glu Leu His Ala Ile Leu Arg Arg Gln Glu Asp Phe Tyr Pro
465                 470                 475                 480
Phe Leu Lys Asp Asn Arg Glu Lys Ile Glu Lys Ile Leu Thr Phe Arg
                485                 490                 495
Ile Pro Tyr Tyr Val Gly Pro Leu Ala Arg Gly Asn Ser Arg Phe Ala
            500                 505                 510
Trp Met Thr Arg Lys Ser Glu Glu Thr Ile Thr Pro Trp Asn Phe Glu
        515                 520                 525
Glu Val Val Asp Lys Gly Ala Ser Ala Gln Ser Phe Ile Glu Arg Met
```

```
                    530                 535                 540
Thr Asn Phe Asp Lys Asn Leu Pro Asn Glu Lys Val Leu Pro Lys His
545                 550                 555                 560

Ser Leu Leu Tyr Glu Tyr Phe Thr Val Tyr Asn Glu Leu Thr Lys Val
                565                 570                 575

Lys Tyr Val Thr Glu Gly Met Arg Lys Pro Ala Phe Leu Ser Gly Glu
                    580                 585                 590

Gln Lys Lys Ala Ile Val Asp Leu Leu Phe Lys Thr Asn Arg Lys Val
                595                 600                 605

Thr Val Lys Gln Leu Lys Glu Asp Tyr Phe Lys Lys Ile Glu Cys Phe
            610                 615                 620

Asp Ser Val Glu Ile Ser Gly Val Glu Asp Arg Phe Asn Ala Ser Leu
625                 630                 635                 640

Gly Thr Tyr His Asp Leu Leu Lys Ile Ile Lys Asp Lys Asp Phe Leu
                    645                 650                 655

Asp Asn Glu Glu Asn Glu Asp Ile Leu Glu Asp Ile Val Leu Thr Leu
                660                 665                 670

Thr Leu Phe Glu Asp Arg Glu Met Ile Glu Glu Arg Leu Lys Thr Tyr
            675                 680                 685

Ala His Leu Phe Asp Asp Lys Val Met Lys Gln Leu Lys Arg Arg Arg
690                 695                 700

Tyr Thr Gly Trp Gly Arg Leu Ser Arg Lys Leu Ile Asn Gly Ile Arg
705                 710                 715                 720

Asp Lys Gln Ser Gly Lys Thr Ile Leu Asp Phe Leu Lys Ser Asp Gly
                    725                 730                 735

Phe Ala Asn Arg Asn Phe Met Gln Leu Ile His Asp Asp Ser Leu Thr
                740                 745                 750

Phe Lys Glu Asp Ile Gln Lys Ala Gln Val Ser Gly Gln Gly Asp Ser
            755                 760                 765

Leu His Glu His Ile Ala Asn Leu Ala Gly Ser Pro Ala Ile Lys Lys
770                 775                 780

Gly Ile Leu Gln Thr Val Lys Val Val Asp Glu Leu Val Lys Val Met
785                 790                 795                 800

Gly Arg His Lys Pro Glu Asn Ile Val Ile Glu Met Ala Arg Glu Asn
                    805                 810                 815

Gln Thr Thr Gln Lys Gly Gln Lys Asn Ser Arg Glu Arg Met Lys Arg
                820                 825                 830

Ile Glu Glu Gly Ile Lys Glu Leu Gly Ser Gln Ile Leu Lys Glu His
            835                 840                 845

Pro Val Glu Asn Thr Gln Leu Gln Asn Glu Lys Leu Tyr Leu Tyr Tyr
850                 855                 860

Leu Gln Asn Gly Arg Asp Met Tyr Val Asp Gln Glu Leu Asp Ile Asn
865                 870                 875                 880

Arg Leu Ser Asp Tyr Asp Val Asp His Ile Val Pro Gln Ser Phe Leu
                    885                 890                 895

Lys Asp Asp Ser Ile Asp Asn Lys Val Leu Thr Arg Ser Asp Lys Asn
                900                 905                 910

Arg Gly Lys Ser Asp Asn Val Pro Ser Glu Glu Val Val Lys Lys Met
            915                 920                 925

Lys Asn Tyr Trp Arg Gln Leu Leu Asn Ala Lys Leu Ile Thr Gln Arg
930                 935                 940

Lys Phe Asp Asn Leu Thr Lys Ala Glu Arg Gly Gly Leu Ser Glu Leu
945                 950                 955                 960
```

```
Asp Lys Ala Gly Phe Ile Lys Arg Gln Leu Val Glu Thr Arg Gln Ile
            965                 970                 975

Thr Lys His Val Ala Gln Ile Leu Asp Ser Arg Met Asn Thr Lys Tyr
            980                 985                 990

Asp Glu Asn Asp Lys Leu Ile Arg Glu Val Lys Val Ile Thr Leu Lys
            995                1000                1005

Ser Lys Leu Val Ser Asp Phe Arg Lys Asp Phe Gln Phe Tyr Lys
        1010                1015                1020

Val Arg Glu Ile Asn Asn Tyr His His Ala His Asp Ala Tyr Leu
        1025                1030                1035

Asn Ala Val Val Gly Thr Ala Leu Ile Lys Lys Tyr Pro Lys Leu
        1040                1045                1050

Glu Ser Glu Phe Val Tyr Gly Asp Tyr Lys Val Tyr Asp Val Arg
        1055                1060                1065

Lys Met Ile Ala Lys Ser Glu Gln Glu Ile Gly Lys Ala Thr Ala
        1070                1075                1080

Lys Tyr Phe Phe Tyr Ser Asn Ile Met Asn Phe Phe Lys Thr Glu
        1085                1090                1095

Ile Thr Leu Ala Asn Gly Glu Ile Arg Lys Arg Pro Leu Ile Glu
        1100                1105                1110

Thr Asn Gly Glu Thr Gly Glu Ile Val Trp Asp Lys Gly Arg Asp
        1115                1120                1125

Phe Ala Thr Val Arg Lys Val Leu Ser Met Pro Gln Val Asn Ile
        1130                1135                1140

Val Lys Lys Thr Glu Val Gln Thr Gly Gly Phe Ser Lys Glu Ser
        1145                1150                1155

Ile Leu Pro Lys Arg Asn Ser Asp Lys Leu Ile Ala Arg Lys Lys
        1160                1165                1170

Asp Trp Asp Pro Lys Lys Tyr Gly Gly Phe Asp Ser Pro Thr Val
        1175                1180                1185

Ala Tyr Ser Val Leu Val Val Ala Lys Val Glu Lys Gly Lys Ser
        1190                1195                1200

Lys Lys Leu Lys Ser Val Lys Glu Leu Leu Gly Ile Thr Ile Met
        1205                1210                1215

Glu Arg Ser Ser Phe Glu Lys Asn Pro Ile Asp Phe Leu Glu Ala
        1220                1225                1230

Lys Gly Tyr Lys Glu Val Lys Asp Leu Ile Ile Lys Leu Pro
        1235                1240                1245

Lys Tyr Ser Leu Phe Glu Leu Glu Asn Gly Arg Lys Arg Met Leu
        1250                1255                1260

Ala Ser Ala Gly Glu Leu Gln Lys Gly Asn Glu Leu Ala Leu Pro
        1265                1270                1275

Ser Lys Tyr Val Asn Phe Leu Tyr Leu Ala Ser His Tyr Glu Lys
        1280                1285                1290

Leu Lys Gly Ser Pro Glu Asp Asn Glu Gln Lys Gln Leu Phe Val
        1295                1300                1305

Glu Gln His Lys His Tyr Leu Asp Glu Ile Ile Glu Gln Ile Ser
        1310                1315                1320

Glu Phe Ser Lys Arg Val Ile Leu Ala Asp Ala Asn Leu Asp Lys
        1325                1330                1335

Val Leu Ser Ala Tyr Asn Lys His Arg Asp Lys Pro Ile Arg Glu
        1340                1345                1350
```

-continued

| | | | | | | | | | | | |
|---|---|---|---|---|---|---|---|---|---|---|---|
| Gln | Ala | Glu | Asn | Ile | Ile | His | Leu | Phe | Thr | Leu | Thr | Asn | Leu | Gly |
| | 1355 | | | | 1360 | | | | 1365 | | |

| Ala | Pro | Ala | Ala | Phe | Lys | Tyr | Phe | Asp | Thr | Thr | Ile | Asp | Arg | Lys |
| | 1370 | | | | 1375 | | | | 1380 | | |

| Arg | Tyr | Thr | Ser | Thr | Lys | Glu | Val | Leu | Asp | Ala | Thr | Leu | Ile | His |
| | 1385 | | | | 1390 | | | | 1395 | | |

| Gln | Ser | Ile | Thr | Gly | Leu | Tyr | Glu | Thr | Arg | Ile | Asp | Leu | Ser | Gln |
| | 1400 | | | | 1405 | | | | 1410 | | |

| Leu | Gly | Gly | Asp | Pro | Lys | Lys | Lys | Arg | Lys | Val | Glu | Asp | Pro | Lys |
| | 1415 | | | | 1420 | | | | 1425 | | |

| Lys | Lys | Arg | Lys | Val | Asp | Thr | Arg | Thr | Arg | Pro | Leu | Glu | Gln | Lys |
| | 1430 | | | | 1435 | | | | 1440 | | |

| Leu | Ile | Ser | Glu | Glu | Asp | Leu | Ala | Ala | Asn | Asp | Ile | Leu | Asp | Tyr |
| | 1445 | | | | 1450 | | | | 1455 | | |

| Lys | Asp | Asp | Asp | Asp | Lys | Val | | | | | | | | |
| | 1460 | | | | 1465 | | | | | | |

<210> SEQ ID NO 3
<211> LENGTH: 3476
<212> TYPE: DNA
<213> ORGANISM: Bacillus thuringiensis

<400> SEQUENCE: 3

```
atggacaaca acccaaacat caacgagtgc atcccgtaca actgcctcag caaccctgag      60
gtcgaggtgc tcggcggtga gcgcatcgag accggttaca cccccatcga catctccctc     120
tccctcacgc agttcctgct cagcgagttc gtgccaggcg ctggcttcgt cctgggcctc     180
gtggacatca tctggggcat ctttggcccc tccagtggga cgccttcct ggtgcaaatc      240
gagcagctca tcaaccagag gatcgaggag ttcgccagga accaggccat cagccgcctg     300
gagggcctca gcaacctcta ccaaatctac gctgagagct ccgcgagtg ggaggccgac      360
cccactaacc cagctctccg cgaggagatg cgcatccagt tcaacgacat gaacagcgcc     420
ctgaccaccg ccatcccact cttcgccgtc cagaactacc aagtcccgct cctgtccgtg     480
tacgtccagg ccgccaacct gcacctcagc gtgctgaggg acgtcagcgt gtttggccag     540
aggtggggct cgacgccgc caccatcaac agccgctaca cgacctcac caggctgatc      600
ggcaactaca ccgaccacgc tgtccgctgg tacaacactg gcctggagcg cgtctggggc     660
cctgattcta gagactggat tcgctacaac cagttcaggc gcgagctgac cctcaccgtc     720
ctggacattg tgtccctctt cccgaactac gactcccgca cctacccgat ccgcaccgtg     780
tcccaactga cccgcgaaat ctacaccaac cccgtcctgg agaacttcga cggtagcttc     840
aggggcagcg cccagggcat cgagggctcc atcaggagcc acacctgat ggacatcctc      900
aacagcatca ctatctacac cgatgcccac cgcggcgagt actactggtc cggccaccag     960
atcatggcct cccggtcgg cttcagcggc ccgagttta cctttcctct ctacggcacg      1020
atgggcaacg ccgctccaca caacgcatc gtcgctcagc tgggccaggg cgtctaccgc      1080
accctgagct ccaccctgta ccgcaggccc ttcaacatcg gtatcaacaa ccagcagctg     1140
tccgtcctgg atgcactga gttcgcctac ggcacctcct caacctgcc ctccgctgtc      1200
taccgcaaga gcggcacggt ggattccctg acgagatcc accacagaa caacaatgtg      1260
cccccaggc agggttttc ccacaggctc agcacgtgt ccatgttccg ctccggcttc       1320
agcaactcgt ccgtgagcat catcagagct cctatgttct cctggattca tcgcagcgcg     1380
gagttcaaca atatcattcc gtcctcccaa atcacccaaa tcccctcac caagtccacc     1440
```

```
aacctgggca gcggcacctc cgtggtgaag ggcccaggct tcacgggcgg cgacatcctg    1500
cgcaggacct ccccgggcca gatcagcacc ctccgcgtca acatcaccgc tcccctgtcc    1560
cagaggtacc gcgtcaggat tcgctacgct agcaccacca acctgcaatt ccacacctcc    1620
atcgacggca ggccgatcaa tcagggtaac ttctccgcca ccatgtccag cggcagcaac    1680
ctccaatccg gcagcttccg caccgtgggt ttcaccaccc ccttcaactt ctccaacggc    1740
tccagcgttt tcaccctgag cgcccacgtg ttcaattccg gcaatgaggt gtacattgac    1800
cgcattgagt tcgtgccagc cgaggtcacc ttcgaagccg agtacgacct ggagagagcc    1860
cagaaggctg tcaatgagct cttcacgtcc agcaatcaga tcggcctgaa gaccgacgtc    1920
actgactacc acatcgacca agtctccaac ctcgtggagt gcctctccga tgagttctgc    1980
ctcgacgaga agaaggagct gtccgagaag gtgaagcatg ccaagcgtct cagcgacgag    2040
aggaatctcc tccaggaccc caatttccgc ggcatcaaca ggcagctcga ccgcggctgg    2100
cgcggcagca ccgacatcac gatccagggc ggcgacgatg tgttcaagga gaactacgtg    2160
actctcctgg gcactttcga cgagtgctac cctacctact tgtaccagaa gatcgatgag    2220
tccaagctca aggcttacac tcgctaccag ctccgcggct acatcgaaga cagccaagac    2280
ctcgagattt acctgatccg ctacaacgcc aagcacgaga ccgtcaacgt gcccggtact    2340
ggttccctct ggccgctgag cgcccccagc ccgatcggca agtgtgccca ccacagccac    2400
cacttctcct tggacatcga tgtgggctgc accgacctga acgaggacct cggagtctgg    2460
gtcatcttca agatcaagac ccaggacggc acgagcgcc tgggcaacct ggagttcctc    2520
gagggcaggg ccccctggt cggtgaggct ctggccaggg tcaagagggc tgagaagaag    2580
tggagggaca gcgcgagaa gctcgagtgg gagaccaaca tcgtttacaa ggaggccaag    2640
gagagcgtcg acgccctgtt cgtgaactcc cagtacgacc gctgcaggc cgacaccaac    2700 atcgccatga tccacgctgc cgacaagagg gtgcacagca ttcgcgaggc ctacctgcct    2760
gagctgtccg tgatccctgg tgtgaacgct gccatctttg aggagctgga gggccgcatc    2820
tttaccgcat tctccctgta cgacgcccgc aacgtgatca agaacggtga cttcaacaat    2880
ggcctcagct gctggaacgt caagggccac gtggacgtcg aggaacagaa caaccaccgc    2940
tccgtcctgg tcgtcccaga gtgggaggct gaggtctccc aagaggtccg cgtctgccca    3000
ggccgcggct acattctcag ggtcaccgct tacaaggagg ctacggtga gggctgtgtg    3060 accatccacg agatcgagaa caacaccgac gagcttaagt tctccaactg cgtggaggag    3120
gaggtgtacc aaacaacac cgttacttgc aacgactaca ccgccaccca ggaggagtac    3180
gagggcacct acacttccag gaacagggc tacgatggtg cctacgagag caacagcagc    3240
gttcctgctg actacgcttc cgcctacgag gagaaggcct acacgatgg ccgcagggac    3300 aacccttgcg agagcaaccg cggctacggc gactacactc ccctgcccgc cggctacgtt    3360
accaaggagc tggagtactt cccggagact gacaaggtgt ggatcgagat cggcgagacc    3420
gagggcacct tcatcgtgga cagcgtggag ctgctcctga tggaggagta gaattc       3476
```

<210> SEQ ID NO 4
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 4

```
gtacaactgc ctcagcaacc ctg                                           23

<210> SEQ ID NO 5
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 5
gcaaccctga ggtcgaggtg ct                                            22

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
ggcggtgagc gcatcgagac                                               20

<210> SEQ ID NO 7
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 7
gctcagcgag ttcgtgcc                                                 18

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
gcatctttgg cccctcccag                                               20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
gggatgcact cgttgatgtt                                               20

<210> SEQ ID NO 10
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 10
gccgagcacc tcgacctc                                                 18

<210> SEQ ID NO 11
<211> LENGTH: 20
<212> TYPE: DNA
<213> ORGANISM: Artificial sequence
```

```
<220> FEATURE:
<223> OTHER INFORMATION: Synthetic oligonucleotide

<400> SEQUENCE: 11
gggagaggga gatgtcgatg                                                20

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 12
gcctggcacg aactcgctga g                                              21

<210> SEQ ID NO 13
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 13
gatgatgtcc acgaggccc                                                 19

<210> SEQ ID NO 14
<211> LENGTH: 1000
<212> TYPE: DNA
<213> ORGANISM: Zea mays

<400> SEQUENCE: 14
tgagagtaca atgatgaacc tagattaatc aatgccaaag tctgaaaaat gcaccctcag    60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga ggggcatca    480 aagatctggc tgtgttttcca gctgtttttg ttagccccat cgaatccttg acataatgat   540
cccgcttaaa taagcaacct cgcttgtata gttccttgtg ctctaacaca cgatgatgat    600
aagtcgtaaa atagtggtgt ccaaagaatt ccaggccca gttgtaaaag ctaaaatgct    660
attcgaattt ctactagcag taagtcgtgt ttagaaatta ttttttata tacctttttt   720 ccttctatgt acagtaggac acagtgtcag cgccgcgttg acggagaata tttgcaaaaa   780
agtaaaagag aaagtcatag cggcgtatgt gccaaaaact tcgtcacaga gagggccata   840
agaaacatgg cccacggccc aatacgaagc accgcgacga agcccaaaca gcagtccgta    900
ggtggagcaa agcgctgggt aatacgcaaa cgttttgtcc caccttgact aatcacaaga   960
gtggagcgta ccttataaac cgagccgcaa gcaccgaatt                        1000

<210> SEQ ID NO 15
<211> LENGTH: 381
<212> TYPE: DNA
<213> ORGANISM: Sorghum bicolor
```

```
<400> SEQUENCE: 15
gcttgctcaa cttagcactt agcagtaaca tttttagtaca ctgattgcga ttgttagcag        60
tactccgggt tagcacctag cagtactccg ggagctctgt gaactgtgaa gagtgaacta       120
caaccatcta ggaatcagct gagcttatta ttatcttacc ttcttttta tcctcaggtg        180 aggcattagc attaagccac caacagggt aaagctaatg cagcatcgat gggctcgacc        240
tgaactctga acttctgaag cccacacata caacaagtgg cccagtgcgc aatatgctgg       300
ccactcccac cgattagtac cacctcggct cctcaaatgc gtagaagcta acttaaaagc       360
tcagttctcc agccattcag c                                                381

<210> SEQ ID NO 16
<211> LENGTH: 2000
<212> TYPE: DNA
<213> ORGANISM: Zea mays

<400> SEQUENCE: 16
cgccgagcaa gtcaatcgcc ccatcatgcg gacttgctcg gcaaatgggc tagagagagg        60
tttatgggcc tcgccttggg taccctgttc ccggtacccg acaatgacct tcctcggatg       120
ctgataggtc aattaaagaa acaacaatgg atatatatgg ataggtatag aggtgtaagg       180
ctatctctag aacgttgcct attcttatac ccatattcaa actttattga taaaatgttg       240
gacaggtctg gtgcccttgg aacaagtgtt gtttccattc tccagagtgg actacttctt       300
gcgctgattt gtttggtgag ttaccgaagg agatttaggg gaagaaaaac agggcactta       360
taagtgatat attgttttatc tcagatgtat tgatcacttc tctggtattg gtgcaatgta       420
ttggggtacc gatcactgag taatcacgca atgtattggg gtactaaatc ctctctggta       480
tcgattattc atgcaatgta ttgacgattt taataagtga atcgccaatg tatatgatat       540
ttccactggc ggtgtactta atacagccgc cagtgtatat acatcatttc cactgacggt       600
tcagttaagt gaaccgcaag tgtatatgac atttccactg gcggtgtact ttatagaacc       660
gccagtgtat atacatcctt tacactgacg gttcagttaa gtgaaccacc agtgtatatg       720
atatttccac tggcggtgta cttaatacag ctgccagtgt atatacatcc tttatactga       780
cggttcagtt aagtgaaccg acagtgtata tgatatttcc actgccggtg tacttaatac       840
agctgccagt gtatatacat cctttatact gacggttcag ttaagtgaac cgccagtata       900
tattatattt ccactggcgg tttacttaat aaaaccgcaa gtgtaaatac atcatttaca       960
ctgacagttt tgttaagtga accaccagcg tatatatatt tacactgccg gttcgttaag      1020
acgggcccgt ctgttttttt cactggcgtg ctgtaactga aaccgccatt ataaatttct      1080
acgtgccgcc accttagagc tctttttctac tagtgttaac ttcttttctt gtagaccatt      1140
tggaaaacag gaaacaacgc ggtactgtat tcaacaacag atggttgtcc acacctatga      1200
caatcatggc gtcaatgcag tagtaagttt gtcgtttttg tgtgtgtgtg tttattagcc      1260
gtttctttgt tttttttctt ctgttgagct ccaactttat gaaacgtcgt aagctggtaa      1320
ttatgaaatg taaggatttg gagagagaaa aaaacgggga gggaaaacca tgcatgctgc      1380
tgacgcgacg gccggacgca gacgcaacaa tgccccccggt gcggcgttgt cgagcagcca      1440
ctgcaccacc ccacgcatca cctgcagtaa tctagcgacg ggttttttctt atttatttat      1500 ttatttattt atttttcttc tctccctccc tccctcagat ttgttttcgt tttcattaat      1560
cgttattacc agcaattaat taactttatc tattgattta ccaaaccgca ataaagaata      1620
tatatattct tttattaagg tccagtaata agcagcacag aagcgcaggt gcagcagcag      1680
```

```
cagcgtcagc gcccgaggcg cgcacgagag aaacagaggc tgacgaggtg gggcccgtgc    1740
gggccttgac caatcggagt tcgacaacag cctggccacc cacaaacaca cactccttcg    1800
cctcgcgccg gccgtcgtcg cctccctcca ccgaacgatc cctcctcctc ctcctcctcc    1860
tcctcctcgc atcccacccc accccacctt ctccttaaag ctacctgcct acccggcggt    1920
tgccgccgcc gcaatcgatc gaccggaaga gaaagagcag ctagctagct agcagatcgg    1980
agcacggcaa caaggcgatg                                                2000
```

METHODS FOR GENETIC MODIFICATION OF PLANTS

RELATED APPLICATIONS

This application is a 371 National Stage application of International Application No. PCT/US2016/064733, filed Dec. 2, 2016, which claims benefit of U.S. Provisional Application Ser. No. 62/261,944, filed Dec. 2, 2015, entitled CRISPR-GENERATED TRAITS IN PLANTS, the contents of which are hereby incorporated by reference in their entirety.

TECHNICAL FIELD

This document relates to methods and materials for the genetic modification of plants involving specific gene targeting and precise editing of nucleic acid sequences in a plant (e.g. a crop plant).

SEQUENCE LISTING

The instant application includes a sequence listing in electronic format submitted to the United States Patent and Trademark Office via the electronic filing system. The ASCII text file, which is incorporated-by-reference herein, is titled "CRES031WO_ST25" was created on Dec. 2, 2016, and has a size of 29.4 kilobytes.

BACKGROUND

The new methods for efficient directed genome editing have been developed, including CRISPR. The edited mutations are usually inherited in the germline and necessarily impact an entire life cycle. Heritably modifying a plant genome is not always desirable. A mutation can have pleiotropic effects, with desirable and undesirable aspects of the resulting phenotype.

SUMMARY

Provided herein are methods and materials for producing plants having desirable agronomic traits. The methods can comprise crossing a first transgenic plant with a second transgenic plant, wherein the first transgenic plant comprises a first nucleic acid molecule comprising an ubiquitously expressing promoter linked to a first transgene encoding at least one gRNA (guide RNA), wherein the gRNA comprises a targeting sequence that hybridizes to a portion of at least one gene, and wherein the second transgenic plant comprises a second nucleic acid molecule comprising a reproductive tissue specific promoter operably linked to a second transgene that encodes a Cas enzyme, obtaining one or more progeny plants produced from the crossing; and selecting a F2 or later progeny plant having the desirable agronomic trait or a seed thereof. Said selecting may comprise collecting a plurality of F2 seed produced by the one or more progeny plants; and screening the plurality of F2 seed or plant tissue grown from the plurality of F2 seed for presence of the desirable agronomic trait. Said screening may comprise identifying a genomic sequence carrying a mutation responsible for the desirable agronomic trait.

In certain embodiments, the ubiquitously expressing promoter can include a pol III promoter. The ubiquitously expressing promoter is a Sorghum U3 promoter. In addition, the ubiquitously expressing promoter comprises a nucleic acid molecule can have at least 90% sequence identity to SEQ ID NO: 15 or a fragment thereof having the promoter activity of SEQ ID NO: 15.

In certain embodiments, the reproductive tissue specific promoter is a non-embryonic reproductive tissue specific promoter. The reproductive tissue specific promoter can be a developmental-specific promoter or an inducible promoter. For example, the inducible promoter can be induced by the presence of an antibiotic or a hormone. In certain embodiments, the reproductive tissue specific promoter may be a floral meristem promoter. For example, the reproductive tissue specific promoter may be a promoter of a Zap1a, Zap1b, ZLF1, ZLF2, or ZMM4 endogenous gene. In addition, the reproductive tissue specific promoter can comprise a nucleic acid molecule comprising the nucleic acid sequence of SEQ ID NO: 16, or comprising a nucleic acid sequence having at least 90% sequence identity to SEQ ID NO: 16 or a fragment thereof having the promoter activity of SEQ ID NO: 16 in certain embodiments.

In certain embodiment, the Cas enzyme may be selected from the group consisting of Cas9, Cas6, and Cpf1.

In particular embodiments, the gene is an endogenous gene. For example, the plant has reduced expression of the endogenous gene; the plant has eliminated expression of the endogenous gene; or the plant has increased expression of the endogenous gene.

In certain embodiments, the endogenous gene can encode a polypeptide involved in a cell wall polysaccharides pathway. For example, the endogenous gene polypeptide involved in a cell wall polysaccharides pathway is selected from the group consisting of a polypeptide involved in the lignin pathway and a polypeptide involved in cellulose synthase. For example, the polypeptide involved in the lignin pathway is selected from the group consisting of phenylalanine ammonia-lyase (PAL), cinnamate 4-hydroxylase (C4H, 4-coumarate:coa ligase (4CL), p-coumarate 3-hydroxylase (C3H), p-hydroxycinnamoyl-coa:quinate/shikimate p-hydroxycinnamoyltransferase (HCT), caffeoyl-coa o-methyltransferase (CCOAOMT), cinnamoyl-coa reductase (CCR), ferulate 5-hydroxylase (F5H), caffeic acid o-methyltransferase (COMT), and cinnamyl alcohol dehydrogenase (CAD).

In particular embodiments, the endogenous gene encodes a polypeptide involved in hormone biosynthesis. For example, the polypeptide that is involved in hormone biosynthesis is selected from the group consisting of the gibberellin (GA) pathway, the brassinosteroids (BR) pathway, the indole-3-acetic acid (IAA) pathway, the jasmonic acid (JA) pathway, the abscisic acid (ABA) pathway, the salicylic acid (SA) pathway, the cytokinin pathway, and the ethylene pathway. For example, the polypeptide can be involved in the GA pathway is selected from the group consisting of GA20-oxidase, GA3-oxidase, GA2-oxidase, and gibberellin insensitive dwarf (GID). In certain embodiments, the endogenous gene encodes a protein that represses cell division. For example, the protein represses cell division is a cyclin. In other embodiments, the at least one gene is a transgene.

In particular embodiments, the first and/or the second transgenic plant comprise at least one third transgene that imparts a further desirable agronomic trait to the plant. For example, the third transgene encodes a polypeptide that imparts herbicide tolerance to the plant. For instance, the polypeptide that imparts herbicide tolerance to the plant is selected from the group consisting of phosphinothricin acetyl transferase (PAT), bialaphos resistance (BAR), 5-enolpyruvyl-3-phosphoshikimate synthase (EPSPS), acetolactate synthase (ALS), acetyl coenzyme A carboxylase (ACCase), dicamba mono-oxygenase (DMO), aryloxyalkanoate dioxygenase-12 (aad-12), and 4-hydroxyphenylpyruvate dioxygenase (HPPD). In particular embodiments, the transgene encodes a polypeptide that imparts insect resistance to the plant. For example, the polypeptide that imparts insect resistance to the plant is selected from the group consisting of Cry1Ab, Cry1Ac, Cry1A.105, Cry1F, Cry2Ab, Cry3Bb1, Cry34Ab1, Cry35Ab1, mCry3A, and VIP3. The third transgene can encode a polypeptide that imparts pathogen resistance or is a product quality trait. In various embodiments, the further desirable agronomic trait is selected from the group consisting of increased yield, drought tolerance, cold tolerance, tolerance to environmental stresses, enhanced nitrogen use, and male sterility. For example, the pathogen resistance is selected from the group consisting of virus, fungus, bacterium, and nematode resistance. The product quality trait can be selected from the group consisting of delayed fruit ripening, altered amino acid profile, altered oil profile, modified seed storage proteins, enhanced floral characteristics for ornamentals, and increased solids in fruit. In certain embodiments, the third transgene can encode a cell wall polypeptide.

In certain embodiments, the plant can be a member of a species selected from the group consisting of *Brassica, Carthamus, Glycine, Gossypium, Helianthus, Jatropha, Parthenium, Populus, Ricinus, Elaeis, Festuca, Hordeum, Lolium, Oryza, Panicum, Pennisetum, Phleum, Poa, Saccharum, Secale, Sorghum, Triticosecale, Triticum*, and *Zea*. For example, the plant can be selected from the group consisting of *Panicum virgatum, Sorghum bicolor, Miscanthus giganteus, Zea mays, Glycine max, Brassica napus, Triticum aestivum, Gossypium hirsutum, Oryza sativa, Helianthus annuus, Medicago sativa, Beta vulgaris*, and *Pennisetum glaucum*.

In certain aspects, this document describes plant or seed produced by the method. And in certain aspects, the progeny plants can comprise a genetic mechanism to eliminate expression of an endogenous gene or a transgene in reproductive tissue, wherein the expression of the endogenous gene or the transgene is not eliminated in non-reproductive tissue.

Provided herein are also materials and methods for specific gene targeting and precise editing of nucleic acid sequences in a plant (e.g. a crop plant) using the cluster regularly interspaced short palindromic repeats (CRISPR) associated nuclease (Cas) system. For example, materials and methods provided herein can be used to specifically target at least one gene (e.g., an endogenous gene or a transgene) to reduce or eliminate function of the target gene in a particular tissue of the plant or at a particular stage of development.

The materials and methods provided herein can be used one to edit the plant genome in a manner that controls the expression of endogenous genes and/or controls the transmission and expression of transgenic traits.

This document provides transgenic plants. In one aspect, this document provides transgenic plants containing a first nucleic acid molecule and a second nucleic acid molecule. For example, a transgenic plant can contain a first nucleic acid molecule comprising a first promoter operably linked to a first transgene, wherein the first transgene encodes at least one gRNA, wherein the gRNA comprises a targeting sequence that can hybridize to a portion of at least one endogenous gene, and a second nucleic acid molecule comprising a second promoter operably linked to a second transgene, wherein the second transgene encodes a Cas enzyme (e.g., Cas9, Cas6, or Cpf1). For example, a first plant can include a first nucleic acid molecule comprising a first promoter operably linked to a first transgene, wherein the first promoter is ubiquitously-expressed promoter and wherein the first transgene encodes at least one gRNA. For example, a second plant can include a second nucleic acid molecule comprising a second promoter operably linked to a second transgene, wherein the second promoter is a tissue-specific or developmental-specific promoter and wherein the second transgene encodes a Cas enzyme.

In one aspect, this document provides plants having reduced expression of at least one endogenous gene, wherein the plant includes a mutation in the at least one endogenous gene, a first nucleic acid molecule comprising a first promoter operably linked to a first transgene, wherein the first transgene encodes at least one gRNA, wherein the gRNA comprises a targeting sequence that can hybridize to a portion of the at least one endogenous gene, and a second nucleic acid molecule comprising a second promoter operably linked to a second transgene, wherein the second transgene encodes a Cas enzyme (e.g., Cas9, Cas6, or Cpf1). In some cases, the first promoter can be a ubiquitously-expressed promoter (e.g., a pol III promoter). In some cases, the second promoter can be a tissue-specific promoter (e.g., specific for stem, leaf, root, shoot, or flower tissue), a developmental-specific promoter (e.g., specific for an embryonic, a vegetative, a shoot apical meristem, a floral meristem, or a root meristem developmental stage), or an inducible promoter (e.g., in the presence of an antibiotic or a hormone). In some cases, the endogenous gene can encode a polypeptide involved in elaborating cell wall polysaccharides. For example, the polypeptide involved in elaborating cell wall polysaccharides can be a polypeptide involved in the lignin pathway (e.g., phenylalanine ammonia-lyase (PAL), cinnamate 4-hydroxylase (C4H, 4-coumarate:coa ligase (4CL), p-coumarate 3-hydroxylase (C3H), p-hydroxycinnamoyl-coa:quinate/shikimate p-hydroxycinnamoyltransferase (HCT), caffeoyl-coa o-methyltransferase (CCOAOMT), cinnamoyl-coa reductase (CCR), ferulate 5-hydroxylase (F5H), caffeic acid o-methyltransferase (COMT), or cinnamyl alcohol dehydrogenase (CAD)) or a polypeptide involved in cellulose synthase. In some cases, the endogenous gene can encode a polypeptide involved in hormone biosynthesis. For example, the polypeptide involved in hormone biosynthesis can be in the gibberellin (GA) pathway (e.g., GA20-oxidase, GA3-oxidase, GA2-oxidase, or gibberellin insensitive dwarf (GID)), the brassinosteroids (BR) pathway, the indole-3-acetic acid (IAA) pathway, the jasmonic acid (JA) pathway, the abscisic acid (ABA) pathway, the salicylic acid (SA) pathway, the cytokinin pathway, or the ethylene pathway. In some cases, the endogenous gene can encode a protein that represses cell division (e.g., a cyclin).

In one aspect, this document provides plants including a genetic mechanism to eliminate expression of a third transgene, wherein the third transgene imparts a desirable trait to the plant. A plant including a genetic mechanism to eliminate expression of a third transgene can include a first nucleic acid molecule comprising a first promoter operably linked to a first transgene, wherein the first transgene comprises at least one gRNA, wherein the gRNA comprises a targeting sequence that can hybridize to a portion of the third transgene, and a second nucleic acid comprising a second promoter operably linked to a second transgene, wherein the second transgene encodes a Cas enzyme (e.g., Cas9, Cas6, and Cpf1), wherein the second promoter is a tissue-specific promoter or a developmentally-specific promoter. In some cases, the first promoter is a ubiquitous promoter (e.g., a pol III promoter). In some cases, the tissue-specific promoter or the developmentally-specific promoter is a non-embryonic reproductive tissue (e.g., a floral meristem promoter). In some cases, the third transgene encodes a polypeptide that imparts herbicide tolerance to the plant (e.g., phosphinothricin acetyl transferase (PAT), bialaphos resistance (BAR), 5-enolpyruvyl-3-phosphoshikimate synthase (EPSPS), acetolactate synthase (ALS), acetyl coenzyme A carboxylase (ACCase), dicamba mono-oxygenase (DMO), aryloxyalkanoate dioxygenase-12 (aad-12), or 4-hydroxyphenylpyruvate dioxygenase (HPPD)). In some cases, the third transgene encodes a polypeptide that imparts insect resistance to the plant (e.g., Cry1Ab, Cry1Ac, Cry1A.105, Cry1F, Cry2Ab, Cry3Bb1, Cry34Ab1, Cry35Ab1, mCry3A, or VIP3). In some cases, the third transgene encodes a polypeptide that imparts or effects an agronomic trait (e.g., increased yield, drought tolerance, cold tolerance, tolerance to environmental stresses, enhanced nitrogen use, or male sterility), pathogen resistance (e.g., virus, fungus, bacterium, or nematode resistance), or product quality trait (e.g., delayed fruit ripening, altered amino acid profile, altered oil profile, modified seed storage proteins, enhanced floral characteristics for ornamentals, or increased solids in fruit). In some cases, the third transgene encodes a cell wall polypeptide.

In some cases, the plant can be a member of a species of *Brassica, Carthamus, Glycine, Gossypium, Helianthus, Jatropha, Parthenium, Populus, Ricinus, Elaeis, Festuca, Hordeum, Lolium, Oryza, Panicum, Pennisetum, Phleum, Poa, Saccharum, Secale, Sorghum, Triticosecale, Triticum,* or *Zea*. For example, the plant can be a *Panicum virgatum, Sorghum bicolor, Miscanthus giganteus, Zea mays, Glycine max, Brassica napus, Triticum aestivum, Gossypium hirsutum, Oryza sativa, Helianthus annuus, Medicago sativa, Beta vulgaris,* or *Pennisetum glaucum*. This document also provides seeds made by said plants.

This document also provides methods of making and using transgenic plants. In one aspect, this document provides methods of producing a plant having reduced expression of at least one endogenous gene. For example, a method of producing a plant having reduced expression of at least one endogenous gene can include crossing a first plant with a second plant, wherein the first plant comprises a first nucleic acid molecule comprising a first promoter operably linked to a first transgene, wherein the first transgene encodes at least one gRNA, wherein the gRNA comprises a targeting sequence that can hybridize to a portion of the at least one endogenous gene, wherein the second plant comprises a second nucleic acid molecule comprising a second promoter operably linked to a second transgene, wherein the second transgene encodes a Cas enzyme; wherein progeny plants exhibit reduced expression of the least one endogenous gene.

In one aspect, this document provides methods of producing seed. For example, a method of producing seed can include crossing a first plant with a second plant, wherein the first plant comprises a first nucleic acid comprising a first promoter operably linked to at least one gRNA-expressing transgene, wherein the gRNA hybridizes to the at least one transgene, wherein the second plant comprises a second nucleic acid comprising a second promoter operably linked to a Cas-expressing transgene, wherein either the first or the second plant comprises a third transgene that imparts a desirable agronomic trait to the plant, and collecting progeny seed, wherein the progeny seed comprises a genetic mechanism to eliminate expression of the third transgene in a particular tissue or at a particular developmental stage in a plant grown from the seed.

In one aspect, this document provides methods of screening for plants having a desirable agronomic trait. For example, a method of screening for plants having a desirable agronomic trait can include crossing a first plant with a second plant, wherein the first plant comprises a first nucleic acid molecule comprising a first promoter operably linked to a first transgene, wherein the first transgene encodes a plurality of gRNAs, wherein the second plant comprises a second nucleic acid molecule comprising a second promoter operably linked to a second transgene, wherein the second transgene encodes a Cas enzyme, thereby producing mutant progeny plants, and screening the mutant progeny plants for the desirable agronomic trait. In some cases, a method of screening for plants having a desirable agronomic trait can also include identifying the genomic sequence carrying the mutation in the mutant progeny plants.

This document also provides plant expression vectors. In some cases, a plant expression vector can include a promoter of Sorghum U3 (SEQ ID NO: 15) operably linked to at least one gRNA-expressing transgene.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 shows a first transgenic parent having a transgene made up of a ubiquitously expressing Pol III promoter that drives the expression of a guide RNA (gRNA) directed to a target gene sequence to be knocked out. A second transgenic parent has a transgene made up of a reproductive tissue specific promoter (RSP) driving the expression of Cas9. A chimeric mutant is made by crossing the two parents. This progeny does not express Cas9 in vegetative tissues, which will therefore maintain the wild type genotype. Its reproductive tissues, on the other hand, will combine the expression of both Cas9 and gRNA, and thus the target sequence of the gRNA will accumulate mutations in the RSP-expressing cells and their progeny.

DETAILED DESCRIPTION

This document provides materials and methods relating to specific gene targeting and precise genome editing in a plant (e.g., a crop plant) using a CRISPR/Cas system.

Transgenic plants provided herein can have at least one nucleic acid molecule having a promoter operably linked to at least one transgene. Transgenic plants having at least one nucleic acid molecule having a promoter operably linked to at least one transgene typically do not exhibit a phenotype based on expression of the at least one nucleic acid molecule. A first transgenic plant having a first nucleic acid molecule having a first promoter (e.g., a ubiquitous promoter) operably linked to at least one first transgene (e.g., a gRNA-expressing transgene) and a second transgenic plant having a second nucleic acid molecule having a second promoter (e.g., a tissue-specific promoter) operably linked to a second transgene (e.g., a Cas-expressing transgene) can be crossed to produce mutant progeny including both the first and the second nucleic acid molecules. Transgenic plants having at least two nucleic acid molecules can have reduced or eliminated function of a target gene (e.g., an endogenous gene or a transgene).

Methods provided herein can be used to control the expression of endogenous genes, control the transmission and expression of transgenic traits, and/or produce a trait in a plant.

I. Nucleic Acid Molecules

This document provides transgenic plants having at least one nucleic acid molecule having a promoter operably linked to at least one transgene. In some embodiments, a transgenic plant can be a parent plant including a nucleic acid molecule having a first promoter operably linked to at least one transgene. For example, a first parent plant can include a first nucleic acid molecule having a first promoter (e.g., a ubiquitous promoter such as Pol III) operably linked to at least one gRNA-expressing transgene, and a second parent plant can include a second nucleic acid molecule having a second promoter (e.g., a tissue-specific promoter) operably linked to a Cas-expressing transgene. It is typically desired, but not necessary, that the at least one transgene does not cause any phenotype in the parent plant.

First and second plants described herein can be crossed (e.g., sexually crossed) to obtain transgenic seed. Transgenic seed produced by crossing a first parent plant and second parent plant as described herein as well as transgenic plants growing from those transgenic seed (i.e., progeny plants) can include both a gRNA as described herein and a Cas as described herein. In some embodiments, transgenic plants can be progeny of crossing a first parent plant and a second parent plant as described herein such that a progeny transgenic plant includes both a first nucleic acid molecule having a first promoter (e.g., a ubiquitous promoter such as a pol III promoter) operably linked to at least one gRNA-expressing transgene, and a second nucleic acid molecule having a second promoter (e.g., a tissue-specific promoter) operably linked to a Cas-expressing transgene. Expression of both a gRNA and a Cas allows for the formation of a gRNA/Cas complex capable of introducing a double strand break in a target site within a genome (e.g., within a gene). The double stranded break can be used to introduce at least one mutation in a gene such that the mutation confers reduced or eliminated function of that gene. Progeny transgenic plants have reduced or eliminated function of a gene (e.g., an endogenous gene or a transgene) as described herein.

Preparation of the nucleic acids disclosed herein can be accomplished using techniques in molecular biology, biochemistry, chromatin structure and analysis, computational chemistry, cell culture, recombinant DNA, and related fields. These techniques are described, for example, in Sambrook et al. *Molecular Cloning: A Laboratory Manual,* 2nd ed., Cold Spring Harbor Laboratory Press, 1989; and in Ausubel et al., *Current Protocols In Molecular Biology*, John Wiley & Sons, New York, 1987.

A. CRISPR-Associated (Cas) Genes

CRISPR/Cas systems are known in the art and can be engineered for directed genome editing. Cas genes encode RNA-guided DNA endonuclease enzymes capable of introducing a double strand break in a double helical nucleic acid sequence. The Cas enzyme can be directed to make the double stranded break at a target site within a gene using a guide RNA.

This document provides a transgenic plant (e.g., a parent plant or a progeny plant) that includes a nucleic acid molecule having a promoter operably linked to a Cas-expressing transgene. In some embodiments, a transgenic plant provided herein can include a nucleic acid having a promoter (e.g., a tissue-specific promoter) operably linked to a Cas (e.g., a Cas9)-expressing transgene.

A Cas enzyme can be guided by a guide polynucleotide (e.g., a guide RNA) to recognize and introduce a sequence-specific double strand break at a site determined by the guide polynucleotide. A Cas enzyme can be from any appropriate species (e.g., an archaea or bacterial species). For example, a Cas enzyme can be from *Streptococcus pyogenes, Pseudomonas aeruginosa,* or *Escherichia coli.* In some cases, a Cas enzyme can be a type I (e.g., type IA, IB, IC, ID, IE, or IF), type II (e.g., IIA, IIB, or IIC), or type III (e.g., IIIA or IIIB) Cas enzyme. The encoded Cas enzyme can be any appropriate homolog or Cas fragment in which the enzymatic function (i.e., the ability to introduce a sequence-specific double strand break in a double helical nucleic acid sequence) is retained. In some embodiments, a Cas enzyme is a *Streptococcus pyogenes* Cas9 enzyme.

In some cases, a Cas enzyme can be codon optimized for expression in particular cells, such as dicot or monocot plant cells.

A Cas-expressing transgene can include a Cas gene from any appropriate species (e.g., an archaea or bacterial species). For example, a Cas gene can be from *Streptococcus pyogenes, Pseudomonas aeruginosa,* or *Escherichia coli.* See, for example, the CRISPR/Cas profiles database available on the National Center for Biotechnology Information website (available at ncbi.nih.gov/pub/wolf/_suppl/CRISPRclass/crisprPro.html). In some embodiments, a Cas gene is from *Streptococcus pyogenes.* Examples of Cas genes that can be used as described herein include, without limitation, Cas3, Cas4, Cas6, Cas8a, Cas8b, Cas8c, Cas9, Cas10, Cas10d, Cmr5, Cpf1 (Zetsche et al., 2015 *Cell* "Cpf1 Is a Single RNA-Guided Endonuclease of a Class 2 CRISPR-Cas System" In Press; DOI: http://dx.doi.org/10.1016/j.cell.2015.09.038), Cse1, Csm2, Csn2, and Csy1 genes. In some embodiments, a Cas gene can be a *Streptococcus pyogenes* Cas9 gene (SEQ ID NO: 1).

Any appropriate CRISPR/Cas system can be used as described herein. Examples of CRISPR/Cas systems that can used as described herein include, without limitation, those are described elsewhere (e.g. U.S. Pat. Nos. 8,697,359; 8,771,945; 8,795,965; 8,865,406; 8,871,445; 8,889,356; 8,889,418; 8,895,308; 8,906,616; 8,932,814; 8,945,839; 8,993,233; 8,999,641; 9,115,348; U.S. Pat. App. Pub. Nos. 2011/0223638; 2014/0068797; 2014/0302563; 2014/0315985; 2015/0152398; 2015/0284697; and Schaeffer et al. 2015 *Plant Sci.* 240:130-42).

This document also provides constructs for expressing a nucleic acid having a promoter operably linked to one or more Cas-expressing transgenes. For example, a construct can be a nucleic acid vector that includes a tissue-specific promoter operably linked to a Cas-expressing transgene. In some embodiments, a construct can be a nucleic acid vector that includes a Zm Zap1 promoter (SEQ ID NO: 16) operably linked to a Cas9-expressing transgene (SEQ ID NO: 1).

B. gRNA Target Sequences

This document provides a transgenic plant (e.g., a parent plant or a progeny plant) that includes a nucleic acid having a promoter operably linked to at least one gRNA-expressing transgene. Expressed gRNAs can target particular nucleic acid sequences (e.g., an endogenous gene or a transgene) at which a Cas enzyme can induce a double stranded break. In some embodiments, a transgenic plant can include a nucleic acid having a promoter (e.g., a ubiquitous promoter) operably linked to at least one gRNA-expressing transgene.

A gRNA can include a gRNA scaffold sequence and a gRNA targeting sequence, and can be designed to target a nucleic acid sequence within the genetic material of a plant (including genomic, transgenic, choloroplastic, or mitochondrial sequences).

A gRNA scaffold sequence can bind a Cas enzyme (e.g., Cas9) thus guiding the Cas enzyme to a target site at which a double stranded break is desired. See, e.g., Ran et al. (2013 Nat Protoc. 8(11):2281-2308).

A gRNA targeting sequence can be a nucleic acid sequence that can hybridize to a target sequence within the genetic material of a plant (e.g., a gene within a plant). In some cases, a gRNA targeting sequence can hybridize a coding or a noncoding strand of a target gene; thus, a gRNA targeting sequence can include a portion of a target gene or a nucleic acid sequence complementary to a portion of a target gene. Hybridization refers to a reaction in which one or more nucleotides react to form a complex that is stabilized via hydrogen bonding between the bases of the nucleotide residues. A gRNA targeting sequence that hybridizes to a target gene can be of any appropriate length that is sufficient to promote hybridization, a double stranded break, and double stranded break repair (e.g., nonhomologous end joining) at the desired site. In some cases, the gRNA targeting sequence can include a portion of a target gene or the full length of a target gene. A gRNA targeting sequence can be from about 5 to about 45 nucleotides in length (e.g., from about 5 to about 45, from about 8 to about 40, from about 10 to about 35, from about 13 to about 30, from about 15 to about 27, from about 17 to about 25, from about 18 to about 24, or from about 19 to about 23 nucleotides in length). For example, the gRNA targeting sequence can be at least 5, at least 8, at least 10, at least 13, at least 15, at least 17, at least 18, at least 19, or at least 20 nucleotides in length. For example, the gRNA targeting sequence can be no greater than 45, no greater than 40, no greater than 35, no greater than 30, no greater than 27, or no greater than 25 nucleotides in length. In some cases, the gRNA targeting sequence includes 20 nucleotides. The amount of sequence identity shared by a gRNA targeting sequence and a desired site in a target gene can vary. For example, the amount of sequence identity with respect to any sequence recited herein with respect to any disclosed embodiments can be at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity. Methods for determining hybridization conditions (including complementarity and percent sequence identity) that can used as described herein include, without limitation, those are described elsewhere (e.g., Sambrook et al. *Molecular Cloning: A Laboratory Manual*, 2nd ed., Cold Spring Harbor Laboratory Press, 1989; and Ausubel et al., *Current Protocols In Molecular Biology*, John Wiley & Sons, New York, 1987).

In some cases, the methods and materials provided herein (e.g., vectors) can include using multiple gRNAs directed to at least one target site within a gene (e.g., an endogenous gene or a transgene) to reduce or eliminate function of the target gene upon mutagenesis. In some cases, a nucleic acid molecule can have a promoter operably linked to at least one gRNA-expressing transgene (e.g., one, two, three, four, five, six, seven, eight, nine, ten, eleven, twelve, or more gRNA-expressing transgenes). In some cases, a nucleic acid molecule can have a promoter operably linked to five gRNA-expressing transgenes.

Multiple (e.g., two or more) gRNA-expressing transgenes provided herein can be designed to target a single gene or can be designed to target multiple (e.g., two or more) genes. In embodiments where multiple gRNA-expressing transgenes are directed to a single target gene, the gRNA-expressing transgenes can be directed to the same site within the target gene, or the gRNA-expressing transgenes can be directed to different sites within the target gene. In embodiments where multiple gRNA-expressing transgenes are directed to multiple target genes, the gRNA-expressing transgenes can each be directed to an independent target gene.

Multiple (e.g., two or more) gRNAs directed to at least one target site within a gene (e.g., an endogenous gene or a transgene) can be provided via a single nucleic acid molecule (e.g., in tandem expression cassettes) or can be provided via multiple nucleic acid molecules (e.g., on more than one expression cassette). In some cases, a nucleic acid molecule can have five gRNA-expressing transgenes provided via tandem expression cassettes.

One or more gRNA-expressing transgenes provided herein can be used to reduce or eliminate function of a gene (e.g., and endogenous gene or a transgene) in a manner that improves plant health (e.g., to provide desirable agronomic traits). Non-limiting examples of endogenous genes that can be targeted with a gRNA include genes necessary for elaboration of cell wall polysaccharides, genes that are repressors or co-repressors of hormone biosynthesis pathways, genes that bring about critical steps in hormone biosynthesis, and genes that repress cell division.

A gRNA can target one or more genes encoding a polypeptide necessary for elaboration of cell wall polysaccharides. Non-limiting examples of polypeptides necessary for elaboration of cell wall polysaccharides include polypeptides that function in the lignin pathway (e.g., phenylalanine ammonia-lyase (PAL), cinnamate 4-hydroxylase (C4H, 4-coumarate:coa ligase (4CL), p-coumarate 3-hydroxylase (C3H), p-hydroxycinnamoyl-coa:quinate/shikimate p-hydroxycinnamoyltransferase (HCT), caffeoyl-coa o-methyltransferase (CCOAOMT), cinnamoyl-coa reductase (CCR), ferulate 5-hydroxylase (F5H), caffeic acid o-methyltransferase (COMT), and cinnamyl alcohol dehydrogenase (CAD), and polypeptides that function in cellulose synthase.

A gRNA can target one or more genes encoding polypeptides involved in hormone biosynthesis (e.g., repressors and/or critical enzymes). For example, reducing or eliminating the function of a repressor of a hormone biosynthesis pathway can be effective to increase hormone levels. In some cases, a repressor of a hormone biosynthesis pathway can be a co-repressor. For example, reducing or eliminating the function of a polypeptide that brings about critical steps in hormone biosynthesis can be effective to decrease hormone levels. Non-limiting examples of polypeptides involved in hormone biosynthesis include the gibberellin (GA) pathway, the brassinosteroids (BR) pathway, the indole-3-acetic acid (IAA) pathway, the jasmonic acid (JA) pathway, the abscisic acid (ABA) pathway, the salicylic acid (SA) pathway, the cytokinin pathway, and the ethylene pathway. Exemplary targets of the GA pathway include, for example, GA20-oxidase, GA3-oxidase, GA2-oxidase, gibberellin insensitive dwarf (GID), and other polypeptides described in, for example, Park et al. (WO 2013/086499, published Jun. 13, 2013). For example, reduction or elimination of a repressor of the GA pathway (e.g., GA2-oxidase) can be effective to activate the GA response. For example, reduction or elimination of an activator of the GA pathway (e.g., GA20-oxidase) can be effective to repress the GA response. In some embodiments, a gRNA can be designed to target a combination of one or more repressors and/or co-repressors of a hormone biosynthesis pathway and one or more polypeptides that bring about critical steps in hormone biosynthesis.

A gRNA can target one or more genes encoding a polypeptide that represses cell division (e.g., cell cycle regulators). Non-limiting examples of polypeptides that repress cell division include cyclins (e.g., Arabidopsis CDC2aAt, CDC2bAt, CYCB1; 1, and alfalfa CDC2fM and CYCB2; 2, and their homologs in other species) and cyclin-dependent kinase (CDKs).

One or more gRNA-expressing transgenes can be used to reduce or eliminate function of a gene (e.g., and endogenous gene or a transgene) in a manner that enhances biocontainment (e.g., prevent outflow of the transgene into nature). Non-limiting examples of genes that can be targeted with a gRNA include, genes encoding polypeptides causing sterility (e.g., polypeptide involved in seed development), genes encoding herbicide tolerance polypeptides, genes encoding pesticide tolerance (e.g., insect resistance) polypeptides, transgenes encoding polypeptides providing agronomic traits, and transgenes encoding polypeptides involved in cell wall conversion and digestion.

A gRNA can target one or more genes encoding a polypeptide causing sterility. For example, a polypeptide causing sterility can be a polypeptide involved in seed development. Non-limiting examples of polypeptides involved in seed development include FIE, AP2, INO, ANT, the polypeptide encoded by the LEC2 gene, and HAP3-type CCAAT-box binding factor (CBF) subunit.

A gRNA can target one or more genes encoding an herbicide tolerance polypeptide. Herbicide tolerance is also sometimes referred to as herbicide resistance. Non-limiting examples of herbicide tolerance polypeptides include a polypeptide encoded by a polypeptide encoded by a phosphinothricin acetyl transferase (PAT) gene, a bialaphos resistance (BAR) gene, 5-enolpyruvyl-3-phosphoshikimate synthase (EPSPS), acetolactate synthase (ALS), acetyl coenzyme A carboxylase (ACCase), dicamba mono-oxygenase (DMO), aryloxyalkanoate dioxygenase-12 (aad-12), and 4-hydroxyphenylpyruvate dioxygenase (HPPD).

A gRNA can target one or more genes encoding a pesticide tolerance polypeptide. For example, a pesticide tolerance polypeptide can be an insect resistance polypeptide. Non-limiting examples of herbicide tolerance polypeptides include Cry1Ab, Cry1Ac, Cry1A.105, Cry1F, Cry2Ab, Cry3Bb1, Cry34Ab1, Cry35Ab1, mCry3A, and VIP3. In some embodiments, the gRNA targets a corn-optimized Cry1Ab transgene (SEQ ID NO: 3).

A gRNA can target one or more genes encoding a polypeptide conferring a desirable trait. For example, a desirable trait can be an agronomic trait. Non-limiting examples of agronomic traits include increased yield, drought tolerance, cold tolerance, tolerance to environmental stresses, enhanced nitrogen use, and male sterility. Other desirable traits can include, for example, pathogen (e.g., virus, fungus, bacterium, and/or nematode) resistance, and product quality traits (e.g., delayed fruit ripening, altered amino acid profile, altered oil profile, modified seed storage proteins, enhanced floral characteristics for ornamentals, increased solids in fruit).

This document also provides constructs for expressing a nucleic acid having a promoter operably linked to one or more gRNA-expressing transgenes. For example, a construct provided herein can be a nucleic acid vector including a ubiquitous promoter operably linked to a gRNA expressing transgene. In some embodiments, a construct provided herein can be a nucleic acid vector including the promoter of Sorghum U3 (SEQ ID NO: 15) operably linked to at least one gRNA-expressing transgene having a targeting sequence that can hybridize to a corn-optimized Cry1Ab transgene (SEQ ID NO: 3). In some embodiments, a construct provided herein can be a nucleic acid vector including a promoter of corn U6 (SEQ ID NO: 14) operably linked to at least one gRNA-expressing transgene having a targeting sequence that can hybridize to a corn-optimized Cry1Ab transgene (SEQ ID NO: 3).

C. Promoters

A promoter refers to a nucleic acid capable of driving expression of another nucleic acid (e.g., a coding nucleic acid). A promoter is operably linked to another nucleic acid when it is capable of driving expression of that nucleic acid fragment. The choice of promoter to be included in a nucleic acid molecule described herein depends upon several factors, including, but not limited to, efficiency, selectability, inducibility, desired expression level, and cell- or tissue-preferential expression. First and second nucleic acid molecules described herein can include any appropriate promoter.

A promoter used in a first or second nucleic acid molecule as described herein may be homologous or the promoter may be heterologous. A homologous promoter is a promoter derived from the same species. A heterologous promoter is a promoter derived from a different species relative to the plant into which it is being introduced or relative to the plant being made transgenic.

A promoter used in a first or second nucleic acid molecule as described herein may be a native promoter or a composite promoter. A native promoter may also be referred to as a minimal promoter and is a promoter having a single genomic promoter fragment derived from a single gene. A composite promoter is an engineered promoter and can be a synthetic promoter containing a combination of elements from different origins or a recombinant promoter containing a combination of regulatory elements of the same origin, but not natively found together.

A promoter used in a first or second nucleic acid molecule as described herein may be a ubiquitous promoter or a regulated promoter. A ubiquitous promoter may also be referred to as a constitutive promoter and can drive transcription of an operably linked nucleic acid molecule in most cell types at most times. A regulated promoter may also be referred to as a restricted promoter and can drive transcription of an operably linked nucleic acid molecule in response to specific stimuli. Examples of regulated promoters include cell and/or tissue specific promoters (e.g., driving transcription predominantly, but not necessarily exclusively, in one cell type or one tissue type), developmentally specific promoters (e.g., driving transcription based on developmental events), inducible promoters (e.g., driving transcription in response to presence of a specific stimulus), and other promoters that can drive transcription in a plant. It should be understood that some promoters may belong to more than one category of promoter. For example, a promoter that driving transcription in floral meristems can be considered as both a tissue-specific promoter and a developmentally-specific promoter.

Examples of various classes of promoters and additional regulatory regions that can be used as described herein include, without limitation, those described below as well as those described elsewhere (e.g., U.S. patent application Ser. Nos. 10/957,569; 11/058,689; 11/172,703; 11/208,308; 11/274,890; 60/583,609; 60/612,891; 11/097,589; 11/233,726; 11/408,791; 11/414,142; 10/950,321; 11/360,017; PCT/US05/011105; PCT/US05/23639; PCT/US05/034308; PCT/US05/034343; and PCT/US06/038236; PCT/US06/040572; PCT/US07/62762; PCT/US2009/032485; and PCT/US2009/038792).

i. Ubiquitous Promoters

A promoter used as described herein can be a ubiquitous promoter. A promoter can be said to be "ubiquitous" when it drives transcription in many, but not necessarily all, plant tissues. A ubiquitous promoter can be a promoter that recruits an RNA polymerase III (pol III). As used herein, a "pol III promoter" is a promoter that recruits pol III to drive transcription of an operably linked nucleic acid molecule. Non-limiting examples pol III promoters that can be used as described herein include a promoter of U3 (e.g., a promoter from Sorghum U3 (SEQ ID NO: 15)), a promoter of U6 (e.g., promoter of corn of U6 (SEQ ID NO: 14)), a promoter of H1, and a promoter of 7SL. In some embodiments, the promoter is a promoter from Sorghum U3 (SEQ ID NO: 15).

Other examples of ubiquitous promoters that can be used as described herein include cauliflower mosaic virus (CaMV) 35S promoter, plant ubiquitin promoter (Ubi), rice actin 1 promoter (Act-I), maize alcohol dehydrogenase 1 promoter (Adh-1), mannopine synthase (MAS) promoter, 1' or 2' promoters derived from T-DNA of *Agrobacterium tumefaciens*, figwort mosaic virus 34S promoter, actin promoters such as the rice actin promoter, and ubiquitin promoters such as the maize ubiquitin-1 promoter. Yet other examples of ubiquitous promoters include p326, YP0144, YP0190, p13879, YP0050, p32449, 21876, YP0158, YP0214, YP0380, PT0848, and PT0633 promoters.

A ubiquitous promoter used as described herein can be a basal promoter (e.g., the minimal sequence necessary for assembly of a transcription complex required for transcription initiation). Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

ii. Cell Specific and/or Tissue Specific Promoters

A promoter used as described herein can be a cell specific or a tissue specific promoter. A cell specific or tissue specific promoter drives transcription predominantly, but not necessarily exclusively, in one cell type or one tissue type. Non-limiting examples of cell specific and tissue specific promoters include promoters that can drive transcription of an operably linked nucleic acid molecule in a stem, leaf, root, shoot, flower, and/or non-embryonic reproductive tissues of a plant.

Exemplary cell specific and tissue specific promoters include epidermal layer promoters (e.g., *Arabidopsis* MLI promoter), phloem promoters (e.g., AtSUT2 promoter), green tissue promoters (e.g., RuBisCo small subunit promoter), lateral root-primordia promoters, stalk promoters (e.g., alfalfa S2A and S2B), non-embryonic reproductive tissue promoters, and vascular bundle promoters.

A stem promoter may be specific to one or more stem tissues or specific to stem and other plant parts. Stem promoters may have high or preferential activity in, for example, epidermis and cortex, vascular cambium, procambium, or xylem. Examples of stem promoters include YP0018 which is disclosed in US20060015970 and promoters used with CryIA(b) and CryIA(c) (Braga et al. 2003, *Journal of New Seeds* 5:209-221).

Exemplary root promoters include root-preferential promoters (e.g., YP0128, YP0275, PT0625, PT0660, PT0683, PT0758, PT0613, PT0672, PT0688, and PT0837 promoters), (see, e.g., Lam et al., 1989 *Proc. Natl. Acad. Sci. USA,* 86:7890-7894), root cell specific promoters reported by Conkling et al., (1990 *Plant Physiol.,* 93:1203-1211), and the tobacco RD2 promoter.

Non-embryonic reproductive tissues include, for example, promoters that can drive transcription in floral meristems. Exemplary non-embryonic reproductive tissues can be promoters derived from floral transition integrators. For example in corn they can be promoters of Zap1a, Zap1b, ZLF1, ZLF2, or ZMM4 endogenous genes (Dong et al. 2012 *PLoS ONE* 7(8):e43450). In some embodiments, a promoter can be a Zm Zap1 promoter (SEQ ID NO: 16).

In particular embodiments, the promoters employed in the invention may be previously described promoters or promoters described in the Sequence Listing or fragments or variants thereof having least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity thereto. In certain embodiments, the fragments or variants retain the promoter activity of the unaltered promoter.

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell,* 3(10):1051-1061 (1991)), the *Commelina* yellow mottle virus (CoYMV) promoter (Medberry et al., *Plant Cell,* 4(2):185-192 (1992)), and the rice tungro bacilliform virus (RTBV) promoter (Dai et al., *Proc. Natl. Acad. Sci. USA,* 101(2):687-692 (2004)).

Promoters active in photosynthetic tissue drive transcription in green tissues such as leaves and stems. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.,* 35:773-778 (1994)), the Cab-1 promoter from wheat (Fejes et al., *Plant Mol. Biol.,* 15:921-932 (1990)), the CAB-1 promoter from spinach (Lubberstedt et al., *Plant Physiol.,* 104:997-1006 (1994)), the cab1R promoter from rice (Luan et al., *Plant Cell,* 4:971-981 (1992)), the pyruvate orthophosphate dikinase (PPDK) promoter from corn (Matsuoka et al., *Proc. Natl. Acad. Sci. USA,* 90:9586-9590 (1993)), the tobacco Lhcb1*2 promoter (Cerdan et al., *Plant Mol. Biol.,* 33:245-255 (1997)), the *Arabidopsis thaliana* SUC2 sucrose-H+ symporter promoter (Truernit et al., *Planta,* 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

iii. Developmentally Specific Promoters

A promoter used as described herein can be a developmentally specific promoter. A developmentally specific promoter drives transcription based on developmental events in a plant. Non-limiting examples of developmentally regulated promoters include promoters that can drive transcription of an operably linked nucleic acid molecule in embryonic, vegetative, shoot apical meristem, floral meristem, and/or root meristem of a plant.

Embryonic reproductive tissue promoters include, for example, promoters that can drive expression of an operably linked nucleic acid molecule in fruit, ovule, seed, pollen, pistils, female gametophyte, egg cell, central cell, nucellus, suspensor, synergid cell, flowers, embryonic tissue, embryo, zygote, endosperm, integument, seed coat or pollen. Exemplary embryonic reproductive tissue promoters include those derived from seed-genes such as zygote and embryo LEC1; suspensor G564; maize MAC1 (Sheridan, 1996 *Genetics* 142:1009-1020); maize Cat3, (GenBank No. L05934; Abler, 1993 *Plant Mol. Biol.* 22:10131-1038); Arabidopsis viviparous-1, (Genbank No. U93215); Arabidopsis atmycl, (Urao, 1996 *Plant Mol. Biol.* 32:571-57; Conceicao, 1994 *Plant* 5:493-505); *Brassica napus* napin gene family, including napA (GenBank No. J02798; Josefsson, 1987 *JBL* 26:12196-1301; Sjodahl, 1995 *Planta* 197:264-271). Promoters that are active in ovary tissues such as the ovule wall and mesocarp (e.g., a polygalacturonidase promoter, the banana TRX promoter, the melon actin promoter, YP0396, and PT0623) can also be used as described herein. Examples of promoters that are active primarily in ovules include YP0007, YP0111, YP0092, YP0103, YP0028, YP0121, YP0008, YP0039, YP0115, YP0119, YP0120, YP0374, FBP7, and DEFH9. Exemplary nucellus-specific promoters include those described in, for example, Cehn and Foolad (1997 *Plant Mol. Biol.* 35:821-831). Exemplary early meiosis-specific promoters include those described in, for example, Kobayshi et al., (1994 *DNA Res.* 1:15-26) and Ji and Landgridge (1994 *Mol. Gen. Genet.* 243:17-23). Other meiosis-related promoters include the MMC-specific DMC1 promoter and the SYN1 promoter. Other exemplary embryonic reproductive tissue-specific promoters include, for example, those derived from pollen genes (see, e.g., Guerrero, 1990 *Mol. Gen. Genet.* 224:161-168; Wakeley, 1998 *Plant Mol. Biol.* 37:187-192; Ficker, 1998 *Mol. Gen. Genet.* 257:132-142; Kulikauskas, 1997 *Plant Mol. Biol.* 34:809-814; and Treacy, 1997 *Plant Mol. Biol.* 34:603-611) and derived from embryo genes (e.g., *Brassica napus* 2s storage protein, Arabidopsis 2s storage protein, soybean b-conglycinin, *Brassica napus* oleosin 20 kD gene, soybean oleosin A, soybean oleosin B, Arabidopsis oleosin, maize oleosin 18 kD). Yet other exemplary embryonic reproductive tissue promoters include those derived from the following genes: ovule BEL1, central cell FIE1, flower primordia Arabidopsis APETALA1 (AP1), flower Arabidopsis AP2, Arabidopsis flower ufo, and fruit-specific tomato E8. Exemplary endosperm-specific promoters include promoters that drive transcription in maturing endosperm such as the napin promoter, the Arcelin-5 promoter, the phaseolin promoter (Bustos et al., *Plant Cell,* 1(9):839-853 (1989)), the soybean trypsin inhibitor promoter (Riggs et al., *Plant Cell,* 1(6): 609-621 (1989)), the ACP promoter (Baerson et al., *Plant Mol. Biol.,* 22(2):255-267 (1993)), the stearoyl-ACP desaturase promoter (Slocombe et al., *Plant Physiol.,* 104(4):167-176 (1994)), the soybean α' subunit of β-conglycinin promoter (Chen et al., *Proc. Natl. Acad. Sci. USA,* 83:8560-8564 (1986)), the oleosin promoter (Hong et al., *Plant Mol. Biol.,* 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.,* 13:5829-5842 (1993)), the beta-amylase promoter, and the barley hordein promoter. Exemplary embryo sac/early endosperm regulatory promoters drive transcription only in or predominantly in polar nuclei or precursors thereto and/or the central cell and include *Arabidopsis* viviparous-1 (see, GenBank No. U93215); *Arabidopsis* atmycl (see, Urao, *Plant Mol. Biol.,* 32:571-57 (1996); Conceicao, *Plant,* 5:493-505 (1994)); *Arabidopsis* FIE (GenBank No. AF129516); *Arabidopsis* MEA; *Arabidopsis* FIS2 (GenBank No. AF096096); FIE 1.1 (U.S. Pat. No. 6,906,244); maize MAC1 (see, Sheridan, *Genetics,* 142:1009-1020 (1996)); maize Cat3 (see, GenBank No. L05934; Abler, *Plant Mol. Biol.,* 22:10131-1038 (1993)); and barley lipid transfer protein (Ltp1) promoter (*Plant Cell Rep* 20:647-654 (2001)).

Floral meristem promoters include, for example, promoters derived from floral transition integrators. Exemplary floral meristem promoters can be promoters derived from floral transition integrators including, for example, Zap1a, Zap1b, ZLF1, ZLF2, or ZMM4 promoters (Dong et al. 2012 *PLoS ONE* 7(8):e43450).

iv. Inducible Promoters

A promoter used as described herein can be an inducible promoter. An inducible promoter drives transcription in response to presence of a specific stimulus. Inducible promoters drive transcription of an operably linked nucleic acid molecule in response to the presence of exogenous conditions or stimuli that can be artificially controlled. For example, inducible promoters can be regulated by chemical compounds (e.g., nitrogen, tetracycline, steroids, ethanol, jasmonate, salicylic acid, safeners, gibberellic acid and/or ethylene) or by environmental signals (e.g., light, heat, stress, flooding, drought, phytohormones, and/or wounding).

Non-limiting examples of chemically inducible promoters include Es (which drives transcription in response estradiol); PT0863, PT0829, PT0665, and PT0886 (which drives transcription in response to nitrogen); and rd29A (which drives transcription in response to salt; Kasuga et al. (1999) Nature Biotech 17: 287-291).

Non-limiting examples of physically inducible promoters include heat-inducible promoters (e.g., barley Hvhsp17), stress-inducible promoters (e.g., ABA-inducible promoter complex, RD29A promoter), drought-inducible promoters (e.g., YP0380, PT0848, YP0381, YP0337, PT0633, YP0374, PT0710, YP0356, YP0385, YP0396, YP0388, YP0384, PT0688, YP0286, YP0377, PD1367, and PD0901), and shade-inducible promoters (e.g., PR0924 and PT0678).

v. Other Promoters

Other classes of promoters that can be used as described herein include, but are not limited to, shoot-preferential, callus-preferential, trichome cell-preferential, guard cell-preferential such as PT0678, tuber-preferential, parenchyma cell-preferential, and senescence-preferential promoters.

Methods for identifying and characterizing promoter regions in plant genomic DNA include, for example, those described in Jordano et al., 1989 *Plant Cell,* 1:855-866; Bustos et al., 1989 *Plant Cell,* 1:839-854; Green et al., 1988 *EMBO J.* 7, 4035-4044; Meier et al., 1991 *Plant Cell,* 3, 309-316; and Zhang et al., 1996 *Plant Physiology* 110: 1069-1079.

D. Other Nucleic Acid Molecule Components

Nucleic acid molecules described herein can also include additional features. For example, nucleic acid molecules described herein can include additional regulatory regions (in addition to a promoter) and/or additional features can be used to control and/or enhance the CRISPR/Cas system.

Additional regulatory regions include, without limitation, enhancer sequences, response elements, protein recognition sites, inducible elements, protein binding sequences, 5' and 3' untranslated regions (UTRs), an upstream element or an upstream activation region (UAR), transcriptional start sites, termination sequences, polyadenylation sequences, introns, and combinations thereof (see, e.g., Fromm et al., 1989 *The Plant Cell* 1:977-984). It will be understood that more than one regulatory region may be present in a nucleic acid molecule described herein. Regulatory regions can be obtained by chemical synthesis or by subcloning from a nucleotide (e.g., genomic DNA) that includes such a regulatory region. A regulatory region can also include flanking sequences that contain restriction enzyme sites that facilitate subsequent manipulation.

Additional features that can be used to control and/or enhance the CRISPR/Cas system include, for example, protospacer adjacent motifs, spacers (e.g., target spacers), and termination signals (see, e.g., Mali et al., 2013 *Science* 339:823-826).

A gRNA-expressing transgene can include a protospacer adjacent motif (PAM) sequence. Without being bound by theory, it is believed that PAMs to be important for type I (e.g., type IA, IB, IC, ID, IE, or IF) and type II (e.g., IIA, IIB, or IIC) CRISPR-Cas systems, but are not necessary in type III (e.g., IIIA or IIIB) CRISPR-Cas systems. For example, it is believed that a type I or type II Cas enzyme will recognize and cleave a gene sequence having a PAM sequence at the 3'-end. A PAM sequence can be on a coding strand or a non-coding strand of a target gene. A PAM sequence on a coding strand can be, for example, 5'-NGG-3' where N is any nucleotide followed by two guanine (G) nucleotides or 5'-NGA-3' where N is any nucleotide followed by a guanine (G) residue and an adenine (A) residue. A PAM sequence on a non-coding strand can be, for example, 5'-CCN-3' where N is any nucleotide following two cysteine (C) residues. A nucleic acid molecule having a gRNA-expressing transgene as described herein can also include at least one target spacer. Thus, a target spacer corresponding to a sequence upstream of a PAM can be used to ensure binding of a gRNA to a target site within a gene and enable Cas enzyme activity at a nearby cleavage site within the gene.

In embodiments where the target site is a Cry1Ab transgene, a gRNA-expressing transgene having a targeting sequence that can hybridize to a Cry1Ab transgene can include at least one target spacer which corresponds to a sequence upstream of a PAM immediately following a Cry1Ab transgene. The target spacers can include at least one of SEQ ID NOs: 4-13.

Nucleic acid molecules described herein can also include additional features (e.g., regulatory elements) used to control and/or enhance expression of at least one transgene. Regulatory elements used to control and/or express a transgene are known and can include, without limitation, enhancers, introns, polyA tails, reporter genes, selectable markers, a 3' untranslated region, and/or a 5' untranslated region.

II. Transgenic Plants and Methods of Making Transgenic Plants

This document also provides transgenic plants having at least one nucleic acid molecule described herein (e.g., having a promoter operably linked to at least one transgene).

As used herein, a transgenic "plant" can constitute part or all of a whole plant. For example, a plant can include plant cells, explants, seed, plants grown from said seed, and grain having at least one nucleic acid molecule described herein. A transgenic plant also refers to progeny of an initial transgenic plant provided the progeny inherits a nucleic acid molecule described herein.

A. Transgenic Plants

A transgenic plant provided herein can be a parent plant including a nucleic acid molecule having a first promoter operably linked to at least one transgene. A parent plant can include any combination of promoters and transgenes described herein. For example, a first parent plant provided herein can include a first nucleic acid molecule having a first promoter operably linked to at least one first transgene, a second parent plant provided herein can include a second nucleic acid molecule having a second promoter operably linked to a second transgene, and so on. Notably, expression of a first or a second transgene in a parent plant does not cause any phenotype in a parent plant. As such, a parent plant can be chosen based on the absence of any phenotype resulting from expression of the transgene.

A first parent plant can include a first nucleic acid molecule as described herein. For example, a first parent plant can include a first nucleic acid molecule having a first promoter operably linked to at least one first transgene. The first promoter can be a ubiquitous promoter (e.g., a pol III promoter). The first transgene can be a gRNA-expressing transgene. In some embodiments, a first parent plant can include a first nucleic acid molecule having a pol III promoter (e.g., a promoter of Sorghum U3; SEQ ID NO: 15) operably linked to at least one gRNA-expressing transgene having a targeting sequence that can hybridize to a corn-optimized Cry1Ab transgene (SEQ ID NO: 3). The first parent plant including a first nucleic acid molecule having a pol III promoter (e.g., a promoter of Sorghum U3; SEQ ID NO: 15) operably linked to at least one gRNA-expressing transgene having a targeting sequence that can hybridize to a corn-optimized Cry1Ab transgene (SEQ ID NO: 3) can be a Sorghum plant. In some embodiments, a first parent plant can include a first nucleic acid molecule having a pol III promoter (e.g., a promoter of corn U6; SEQ ID NO: 14) operably linked to at least one gRNA-expressing transgene having a targeting sequence that can hybridize to a corn-optimized Cry1Ab transgene (SEQ ID NO: 3). The first parent plant including a first nucleic acid molecule having a pol III promoter (e.g., a promoter of corn U6; SEQ ID NO: 14) operably linked to at least one gRNA-expressing transgene having a targeting sequence that can hybridize to a corn-optimized Cry1Ab transgene (SEQ ID NO: 3) can be a corn plant. Ubiquitous expression of at least one gRNA-expressing transgene in the first parent plant does not produce a phenotype in the first parent plant.

A second parent plant can include a second nucleic acid molecule as described herein. For example, a second parent plant can include a second nucleic acid molecule having a second promoter operably linked to a second transgene. The second promoter can be a regulated promoter (e.g., a tissue-specific promoter or a developmentally-specific promoter). The second transgene can be a Cas-expressing transgene. In some embodiments, a second parent plant can include a second nucleic acid molecule having a developmentally-specific floral meristem Zm Zap1 promoter (SEQ ID NO: 16) operably linked to at least one Cas9-expressing transgene (SEQ ID NO: 1). Expression of at least one Cas9- expressing transgene in, for example, the floral meristems of the second parent plant does not produce a phenotype in the second parent plant.

A transgenic plant can also be a progeny resulting from a cross between a first plant and parent plant as described herein. Progeny include descendants of a particular plant or plant line. Progeny of an instant plant include seed formed on $F_1$, $F_2$, $F_3$, and subsequent generation plants, seeds formed on $BC_1$, $BC_2$, $BC_3$, and subsequent generation plants, or seeds formed on $F_1BC_1$, $F_1BC_2$, $F_1BC_3$, and subsequent generation plants. Seed produced by a transgenic plant can be grown and then selfed (or outcrossed and selfed) to obtain seed homozygous for the transgene of interest. In some cases, progeny plants may be hybrid transgenic progeny having two or more genetically different types of cells (e.g., a first nucleic molecule which is inherited from a first parent plant and/or a second nucleic acid molecule which is inherited from a second parent plant). In some cases, progeny plants may be "chimerically mutated" transgenic progeny having a mosaic of mutations (e.g., gene disruptions introduced by double stranded break repair in tissues where a gRNA-expressing transgene and a Cas-expressing transgene are co-expressed). Progeny can include transgenic seed produced by crossing a first parent plant and second parent plant as described herein as well as transgenic plants grown from those transgenic seed. Seed produced by a transgenic plant can be grown and then selfed (or outcrossed and selfed) to obtain seed having a desired genotype.

Chimerically mutated transgenic seed produced by crossing a first parent plant and second parent plant as described herein, as well as chimerically mutated transgenic plants growing from those seed, include both a first nucleic acid molecule having a first promoter (e.g., a ubiquitous promoter such as, for example a pol III promoter) operably linked to at least one gRNA-expressing transgene, and a second nucleic acid molecule having a second promoter (e.g., a tissue-specific promoter) operably linked to a Cas-expressing transgene.

Transgenic parent plants described herein can be crossed in order to produce transgenic mutant progeny in a tissue-specific manner and/or a developmentally-specific manner, depending on the particular first and/or second promoters used. Where a gRNA-expressing transgene and a Cas-expressing transgene are co-expressed in a mutant progeny a gRNA/Cas complex can be formed. The gRNA/Cas complex can introduce a double stranded break in a target gene (e.g., an endogenous gene or a transgene) in tissues expressing both a gRNA-expressing transgene and a Cas-expressing transgene. Double stranded break repair (e.g., non-homologous end joining) at the target site can induce one or more mutations in the target site.

In some embodiments, mutations can be kept out of the germ cells by avoiding transgene expression in cellular progenitors thus preventing the mutation from becoming heritable. Accordingly, co-expression of the gRNA-expressing transgene and a Cas-expressing transgene can be designed to avoid editing the cells of the gametophytes, the generative or sperms cells in the pollen, or the megaspore mother cell or the egg cell in the embryosac, or the zygote.

The use of a restricted promoter (e.g., a tissue-specific promoter) to drive expression of a gRNA-expressing transgene or a Cas-expressing transgene, results in formation of a gRNA/Cas complex, and thus reduced or eliminated function of a target gene, only in tissues expression both a gRNA-expressing transgene and a Cas-expressing transgene. For example, when a floral meristem promoter (e.g., a Zm Zap1 promoter; SEQ ID NO: 16) drives expression of a Cas-expressing transgene, the mutation, and hence the reduced or eliminated function of a target gene, will occur in only floral meristem tissues.

In some embodiments, parent plants can have multiple copies of their respective transgenes that are genetically unlinked (i.e., segregated in progeny of heterozygous parents). Unlinked transgenes can be used, for example, to mutate targets in subsequent generations. For example, when a gRNA-expressing transgene is used to target a gene (e.g., an endogenous gene or a transgene) encoding herbicide or pest resistance, the gene function may be reduced, but not fully eliminated, such that some resulting chimerically mutated seeds may inherit a functional gene encoding herbicide or pest resistance. If the initial F1 plant also has multiple unlinked copies of gRNA and Cas transgenes, any functional herbicide or pest resistance transgene transmitted to a subsequent generation is also likely to be passed along with some copies of both gRNA and Cas. Consequently, editing of the herbicide or pest transgene would occur in the subsequent generation, minimizing the possibility of permanent escapee. Without multiple copies, an escaped functional transgene would have only a 25% chance of being co-inherited with both the gRNA and Cas of the plant from the initial cross.

B. Methods for Making Transgenic Plants

At least one nucleic acid molecule described herein can be introduced into a plant or plant cell by any appropriate means in order to establish a transgenic plant. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be used in the methods described herein.

A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be used in the methods described herein.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous biomass composition-modulating polypeptide whose expression has not previously been confirmed in particular recipient cells.

Techniques for introducing nucleic acid molecules into monocotyledonous and dicotyledonous plants are known in the art, and include, without limitation, *Agrobacterium*-mediated transformation, viral vector-mediated transformation, electroporation and particle gun transformation, e.g., U.S. Pat. Nos. 5,538,880; 5,204,253; 5,591,616; 6,013,863; and 6,329,571. If a cell or tissue culture is used as the recipient tissue for transformation, plants can be regenerated from transformed cultures by techniques known to those skilled in the art.

C. Growing Transgenic Plants

Transgenic plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

D. Plant Species

A suitable group of plants with which to practice the invention include dicots, such as safflower, alfalfa, soybean, rapeseed (high erucic acid and canola), or sunflower. Also suitable are monocots such as corn, wheat, rye, barley, oat, rice, millet, amaranth, sorghum, Kentucky bluegrass, bluestems, weeping lovegrass, or fescues. Also suitable are vegetable crops or root crops such as broccoli, peas, sweet corn, popcorn, tomato, beans (including kidney beans, lima beans, dry beans, green beans) and the like. Also suitable are fruit crops such as peach, pear, apple, cherry, orange, lemon, grapefruit, plum, mango and palm. Thus, the invention has use over a broad range of plants, including species from the genera *Anacardium, Arachis, Asparagus, Atropa, Avena, Bothriochloa, Brassica, Citrus, Citrullus, Capsicum, Carthamus, Cocos, Coffea, Cucumis, Cucurbita, Daucus, Dichanthium, Elaeis, Eragrostis, Fragaria, Glycine, Gossypium, Helianthus, Heterocallis, Hordeum, Hyoscyamus, Lactuca, Linum, Lolium, Lupinus, Lycopersicon, Malus, Manihot, Majorana, Medicago, Nicotiana, Olea, Oryza, Panicum, Pannesetum, Persea, Phaseolus, Pinus, Pistachia, Pisum, Pyrus, Poa, Prunus, Raphanus, Ricinus, Secale, Senecio, Sinapis, Solanum, Sorghum, Theobromus, Trigonella, Triticum, Vicia, Vitis, Vigna* and *Zea*.

Exemplary species of plant include, without limitation, *Brassica, Carthamus, Glycine, Gossypium, Helianthus, Jatropha, Parthenium, Populus, Ricinus, Elaeis, Festuca, Hordeum, Lolium, Oryza, Panicum, Pennisetum, Phleum, Poa, Saccharum, Secale, Sorghum, Triticosecale, Triticum,* or *Zea* species. For example, a plant or plant cell can be *Panicum virgatum, Sorghum bicolor, Miscanthus giganteus, Zea mays, Glycine max, Brassica napus, Triticum aestivum, Gossypium hirsutum, Oryza sativa, Helianthus annuus, Medicago sativa, Beta vulgaris,* or *Pennisetum glaucum*.

In some embodiments, a plant or plant cell can be *Zea mays, Sorghum bicolor, Triticum aestivum,* or *Oryza sativa*.

III. Methods of Using Transgenic Plants

This document provides methods of reducing or eliminating the expression of at least one gene (e.g., an endogenous gene or a transgene) in a plant and/or methods of producing a plant (e.g., a chimerically mutated plant) having reduced or eliminated function of at least one gene. Reducing or eliminating expression of at least one gene can be done in a tissue-specific or a developmentally-specific manner as described herein. In some embodiments, methods described herein can be used to reduce or eliminate expression of at least one endogenous gene and/or to produce a plant having reduced or eliminated expression of at least one endogenous gene. In some embodiments, methods described herein can be used to reduce or eliminate expression of at least one transgene and/or to produce a plant having a genetic mechanism to reduce or eliminate expression of at least one transgene (e.g., a third transgene). Methods can include, for example, crossing a first plant with a second plant as described herein. For example, a first plant can include a first nucleic acid molecule having a first promoter operably linked to a gRNA-expressing transgene, and a second plant can include a second nucleic acid molecule having a second promoter operably linked to a Cas-expressing transgene. Progeny of such a cross are chimerically mutated transgenic plants (i.e., having a mosaic of mutations in tissues where a gRNA-expressing transgene and a Cas-expressing transgene are co-expressed) having reduced or eliminated expression of the least one gene.

Methods described herein can be used to reduce or eliminate expression of one or more endogenous genes. There is a need to manage beneficial mutagenesis in a developed or developing plant, such that mutations are caused only in the organs where they are desirable. Reducing or eliminating the expression of a gene as described herein by tissue-specifically or developmentally-specifically triggering site-specific mutagenesis can be used to control the expression of endogenous genes. For example, a homozygous knock-out of lignin pathway gene COMT often produces a brown midrib phenotype, with biomass better suited as forage. But, the brown midrib mutants can have lodging problems, and thus inferior agronomic performance. A chimeric mutant knocking out COMT in subset of tissues, such as leaves but not stems, can combine the lodging resistance of wild type with the forage quality of the COMT mutants.

Methods described herein can be used to reduce or eliminate expression of at least one transgene (i.e., a third transgene). For example, reducing or eliminating expression of a third transgene can prevent the third transgene from outcrossing to wild plant populations. A transgene targeted for reduced or eliminated expression can be any transgene that imparts a desirable trait to the plant. Desirable traits can include, for example, herbicide tolerance, insect resistance, an agronomic trait, pathogen resistance, or a product quality trait.

Transgenic plants are now common in the agricultural industry. Transgenes are typically inherited in the germline and so necessarily impact an entire life cycle. However, heritably modifying the genome of a plant is not always desirable. For instance, a mutation can have pleiotropic effects, with desirable and undesirable aspects of the resulting phenotype. Such plants express novel transgenic traits such as insect resistance, stress tolerance, improved oil quality, improved meal quality and heterologous protein production. As more and more transgenic plants are developed and introduced into the environment, it is important to control the undesired spread of transgenic traits from transgenic plants to other traditional and transgenic cultivars, plant species and breeding lines. While physical isolation and pollen trapping border rows have been employed to control transgenic plants under study conditions, these methods are cumbersome and are not practical for many cultivated transgenic plants. Similarly, some "first generation" transgenic traits, such as insect resistance and glyphosate tolerance, are effective during plant growth, but not particularly useful in the developing grain. For some species capable of outcrossing to wild relatives, such as sorghum outcrossing to Johnson grass, it is desirable to eliminate the functional transgene from reproductive structures to prevent outflow into natural populations, which may lead to invasiveness. Reducing or eliminating the expression of at least one transgene as described herein can be used to control the transmission and expression of transgenic traits. Reducing or eliminating expression of at least one transgene as described herein can be used to control beneficial mutagenesis in a developed or developing plant, such that mutations are caused only in the organs where they are desirable.

This document provides methods of producing a trait in a plant. The ability to efficiently and specifically create targeted mutations in the plant genome greatly facilitates the development of many new crop cultivars with improved or novel traits (e.g., agronomic traits such as increased yield, drought tolerance, cold tolerance, tolerance to environmental stresses, enhanced nitrogen use, and male sterility; herbicide tolerance; insect resistance; pathogen resistance; and/or product quality traits). For example, method of producing a trait in a plant can include crossing a first parent plant including a first nucleic acid having a first promoter operably linked to at least one gRNA-expressing transgene, and a second parent plant including a second nucleic acid having a second promoter operably linked to a Cas-expressing transgene as described herein. Chimerically mutated progeny resulting from the crossing (including both the first nucleic acid having a first promoter operably linked to at least one gRNA-expressing transgene and the second nucleic acid having a second promoter operably linked to a Cas-expressing transgene) can be evaluated for a particular trait.

This document provides methods of screening for a plant (e.g., a chimerically mutated plant) having a desirable trait. Desirable traits can include, without limitation, agronomic traits such as increased yield, drought tolerance, cold tolerance, tolerance to environmental stresses, enhanced nitrogen use, and male sterility; herbicide tolerance; insect resistance; pathogen resistance; and/or product quality traits. In some embodiments, methods of screening for a plant having a desirable trait can also include identifying the genomic sequence carrying the mutation in the chimerically mutated progeny plants.

Methods of screening (i.e., selecting) progeny plants (e.g., chimerically mutated plants) to identify those members of the population that have a desired trait or phenotype, or a combination of desired traits or phenotypes are known. Screening can be performed in a greenhouse and/or laboratory and/or in the field. In some cases, screening can be carried out over multiple transformation events. Screening can be carried out over one or more generations, and/or in more than one geographic location. In some cases, transgenic plants can be grown and selected under conditions which induce a desired phenotype or are otherwise necessary to produce or enhance a desired phenotype in a transgenic plant. In some cases, transgenic plants can be grown and selected cultivation conditions, i.e. without an intentionally applied selection pressure. In addition, screening can be applied during a particular developmental stage in which the phenotype is expected to be exhibited by the plant. Screening can be carried out to choose those transgenic plants having a statistically significant difference in yield (e.g., grain, vegetative biomass, or stem sucrose yield) relative to a control plant. Screening can be carried out to choose those transgenic plants having a statistically significant difference in yield level relative to a control plant that lacks the transgene. Screened transgenic plants have an altered phenotype as compared to a corresponding control plant.

Different controls may be appropriate in different cases for the detection of a desired phenotype. Accordingly, controls may be non-transgenic plants, pooled means of a diverse test population, or selected genotypes available for the comparison, such as genotypes comprising subsets of the transgenes tested.

IV. Articles of Manufacture

This document also provides compositions. In some embodiments, a composition can include at least one transgenic plant (e.g., seedling) as described herein. In some embodiments, a composition can include transgenic seed as described herein.

A plant seed composition can contain transgenic seed as described herein. In some embodiments, a plant seed composition can include seed from a first plant including a first nucleic acid molecule having a first promoter (e.g., a ubiquitously-expressed promoter) operably linked to a first transgene (e.g., a guide RNA-expressing transgene) and seed from a second plant including a second nucleic acid molecule having a second promoter (e.g., tissue-specific or developmental-specific promoter) operably linked to a second transgene (e.g., a Cas-expressing transgene). The proportion of seed of each parent plant in a composition is measured as the number of seed of a particular type divided by the total number of seed in the composition, and can be formulated as desired to meet requirements based on geographic location, pollen quantity, pollen dispersal range, plant maturity, choice of herbicide, and the like. Typically, a plant seed composition including seed from a first plant including a first nucleic acid molecule having a first promoter operably linked to a first transgene and seed from a second plant including a second nucleic acid molecule having a second promoter operably linked to a second transgene includes a substantially uniform mixture of seed from the first parent plant and the second parent plant.

A plant seed composition can include seed from a progeny plant including both a first nucleic acid molecule having a first promoter (e.g., a ubiquitously-expressed promoter) operably linked to a first transgene (e.g., a guide RNA-expressing transgene) and a second nucleic acid molecule having a second promoter (e.g., tissue-specific or developmental-specific promoter) operably linked to a second transgene (e.g., a Cas-expressing transgene).

Compositions of described herein can be provided in the form of a kit. For example, a kit can include a container (e.g., a bag, a plant pot, etc.), a package label accompanying the container (e.g., a tag or label), and/or instructions.

A container can be any container suitable for transporting a composition as described herein. For example, a container can be a bag, a plant pot, or any other means of containing the composition.

A package label accompanying the container can be any type of label suitable for including with the container. For example, a label can be secured to the container, a label can be printed on the container, or a label can be inserted within the container. Generally, the label will indicate what is enclosed within the container (e.g., whether the seed therein are a mixture seed (e.g., seed from a first plant and a second plant), or a mixture of plant species. The label may indicate that the plant, or a plant grown from seed have reduced or eliminated function of a particular target gene. The label may indicate the composition contained therein includes transgenes that provide reduced or eliminated function of a particular target gene.

Instructions accompanying the container can be provided on a package label or provided separately from any label included with the container. Instructions can include the same information as a label or may include different and/or additional information. Generally, the instructions will indicate how to use what is enclosed within the container (e.g., guidance on planting and/or growth conditions for the composition). The instructions may provide guidance on selecting a plant, or a plant grown from seed, having reduced or eliminated function of a particular target gene.

The invention will be further described in the following examples, which do not limit the scope of the invention described in the claims.

EXAMPLES

Example 1: CRISPR-Associated Parent Plant

A CAS9 T-DNA is made carrying a transgene to be transferred. The transgene is made up of a promoter sequence Zm Zap1 promoter (SEQ ID NO: 16) fused to the coding sequence of wild-type CAS9 (SEQ ID NO: 1).

Corn is subjected to Agrobacterium-mediated transformation using the CAS9 T-DNA. A transformant with four functional transgene insertions at unlinked genomic locations is selected. The four transgenes are introgressed into elite germplasm, and eventually selfed and selected for homozygosity for the four unlinked transgenes. The elite germplasm also has a corn-optimized Cry1Ab transgene (SEQ ID NO: 3), which is maintained in the converted CAS9 parental line.

Example 2: Guide RNA Parent Plant

Two gRNA T-DNA are made. Each one has five tandem expression cassettes, each cassette is made up of the corn pol III promoter U6 (SEQ ID NO: 14) fused to different gRNAs. The gRNAs have target spacers corresponding to sequences upstream of protospacer adjacent motif (PAM) fused into single gRNA (see the design methods of Mali et al., 2013 *Science* 339:823-826). The target spacers have the sequences shown in SEQ ID NOs: 4-13. The target sequences are designed to mutate the Cry1Ab transgene.

The constructs are transformed into corn germplasm. A transformant with two unlinked functional transgene insertions of each vector transfer cassette is selected. The four transgenes are introgressed into elite germplasm, and eventually selfed and selected for homozygosity of the four unlinked transgenes to make the gRNA parental line.

Example 3: Progeny Seed and Plants

Hybrid seeds are made by crossing the CAS9 parent with the gRNA parent. Seed are planted for the cultivation of a crop. The crop expresses the Cry1Ab transgene and exhibits the insect resistance phenotype. The crop produces grain of the expected yield and quality. The grain, however, does not contain significant traces of a functional Cry1Ab trait transgene.

OTHER EMBODIMENTS

It is to be understood that while the disclosure has been described in conjunction with the detailed description thereof, the foregoing description is intended to illustrate and not limit the scope of the disclosure, which is defined by the scope of the appended claims. Other aspects, advantages, and modifications are within the scope of the following claims.

The invention claimed is:

1. A method of producing a plant having a desirable agronomic trait comprising:
crossing a first transgenic plant with a second transgenic plant,
wherein the first transgenic plant comprises a first nucleic acid molecule comprising an ubiquitously expressing promoter linked to a first transgene encoding at least one gRNA (guide RNA), wherein the gRNA comprises a targeting sequence that hybridizes to a portion of at least one gene, and
wherein the second transgenic plant comprises a second nucleic acid molecule comprising a reproductive tissue specific promoter operably linked to a second transgene that encodes a Cas enzyme, wherein the reproductive tissue specific promoter is floral meristem promoter selected from the group consisting of:
a promoter of a Zap1a, Zap1b, ZLF1, ZLF2, or ZMM4 endogenous gene,
a nucleic acid molecule comprising the nucleic acid sequence of SEQ ID NO: 16, and
a nucleic acid molecule comprising a nucleic acid sequence having at least 90% sequence identity to SEQ ID NO: 16 or a fragment of SEQ ID NO:16 having the promoter activity of SEQ ID NO: 16;
obtaining one or more progeny plants produced from the crossing; and
selecting a F2 or later progeny plant or a seed thereof having the desirable agronomic trait.

2. The method of claim 1, wherein the method further comprises identifying a genomic sequence carrying a mutation responsible for the desirable agronomic trait.

3. The method of claim 1, wherein the progeny plants comprise a genetic mechanism to eliminate expression of an endogenous gene or a transgene in reproductive tissue, wherein the expression of the endogenous gene or the transgene is not eliminated in non-reproductive tissue, and wherein the genetic mechanism to eliminate expression is further defined by the at least one gRNA comprising a targeting sequence that can hybridize to a portion of the endogenous gene or the transgene.

4. The method of claim 1, wherein the ubiquitously expressing promoter is selected from the group consisting of a pol III promoter, a Sorghum U3 promoter, and a nucleic acid molecule having at least 90% sequence identity to SEQ ID NO: 15 or a fragment thereof having the promoter activity of SEQ ID NO: 15.

5. The method of claim 1, wherein the Cas enzyme is selected from the group consisting of Cas9, Cas6, and Cpf1.

6. The method of claim 1, wherein the at least one gene is an endogenous gene.

7. The method of claim 6, wherein the plant has reduced expression of the endogenous gene, wherein the plant has eliminated expression of the endogenous gene, or wherein the plant has increased expression of the endogenous gene.

8. The method of claim 6, wherein the endogenous gene is an endogenous gene that encodes a polypeptide involved in the lignin pathway, and wherein the polypeptide is phenylalanine ammonia-lyase (PAL), cinnamate 4-hydroxylase (C4H, 4-coumarate:coa ligase (4CL), p-coumarate 3-hydroxylase (C3H), p-hydroxycinnamoyl-coa:quinate/shikimate p-hydroxycinnamoyltransferase (HCT), caffeoyl-coa o-methyltransferase (CCOAOMT), cinnamoyl-coa reductase (CCR), ferulate 5-hydroxylase (F5H), caffeic acid o-methyltransferase (COMT), or cinnamyl alcohol dehydrogenase (CAD).

9. The method of claim 1, wherein the at least one gene is a transgene.

10. The method of claim 1, wherein the first and/or the second transgenic plant comprise at least one third transgene that imparts a further desirable agronomic trait to the plant.

11. The method of claim 10, wherein the third transgene encodes a polypeptide that imparts herbicide tolerance to the plant, wherein the polypeptide is phosphinothricin acetyl transferase (PAT), bialaphos resistance (BAR), 5-enolpyruvyl-3-phosphoshikimate synthase (EPSPS), acetolactate synthase (ALS), acetyl coenzyme A carboxylase (ACCase), dicamba mono-oxygenase (DMO), aryloxyalkanoate dioxygenase-12 (aad-12), or 4-hydroxyphenylpyruvate dioxygenase (HPPD);
wherein the third transgene encodes a Cry1Ab, Cry1Ac, Cry1A.105, Cry1F, Cry2Ab, Cry3Bb1, Cry34Ab1, Cry35Ab1, mCry3A, or VIP3 polypeptide; or
wherein the third transgene encodes a polypeptide that imparts pathogen resistance or is a product quality trait.

12. The method of claim 10, wherein the further desirable agronomic trait is selected from the group consisting of increased yield, drought tolerance, cold tolerance, tolerance to environmental stresses, enhanced nitrogen use, and male sterility.

13. The method of claim 11, wherein the pathogen resistance is selected from the group consisting of virus, fungus, bacterium, and nematode resistance.

14. The method of claim 11, wherein the product quality trait is selected from the group consisting of delayed fruit ripening, altered amino acid profile, altered oil profile, modified seed storage proteins, enhanced floral characteristics for ornamentals, and increased solids in fruit.

15. The method of claim 10, wherein the third transgene encodes a cell wall polypeptide.

16. The method of claim 1, wherein the plant is a member of a species selected from the group consisting of *Brassica, Carthamus, Glycine, Gossypium, Helianthus, Jatropha, Parthenium, Populus, Ricinus, Elaeis, Festuca, Hordeum, Lolium, Oryza, Panicum, Pennisetum, Phleum, Poa, Saccharum, Secale, Sorghum, Triticosecale, Triticum*, and *Zea*.

17. The method of claim 1, wherein the plant is selected from the group consisting of *Panicum virgatum, Sorghum bicolor, Miscanthus giganteus, Zea mays, Glycine max, Brassica napus, Triticum aestivum, Gossypium hirsutum, Oryza sativa, Helianthus annuus, Medicago sativa, Beta vulgaris,* and *Pennisetum glaucum.*

18. The method of claim 1, wherein the floral meristem promoter is a promoter of a Zapla, Zap1b, ZLF1, ZLF2, or ZMM4 endogenous gene.

19. The method of claim 1, wherein the floral meristem promoter is a nucleic acid molecule comprising the nucleic acid sequence of SEQ ID NO: 16.

20. The method of claim 1, wherein the floral meristem promoter is a nucleic acid molecule comprising a nucleic acid sequence having at least 90% sequence identity to SEQ ID NO: 16 or a fragment of SEQ ID NO:16 having the promoter activity of SEQ ID NO: 16.

* * * * *